US010646588B2

(12) United States Patent
Wu et al.

(10) Patent No.: US 10,646,588 B2
(45) Date of Patent: May 12, 2020

(54) RP2 AND RPGR VECTORS FOR TREATING X-LINKED RETINITIS PIGMENTOSA

(71) Applicant: The United States of America, as represented by the Secretary, Department of Health and Human Services, Chicago, IL (US)

(72) Inventors: Zhijian Wu, Gaithersburg, MD (US); Anand Swaroop, Gaithersburg, MD (US); Suddhasil Mookherjee, Rockville, MD (US); Suja Hiriyanna, Boyds, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 60 days.

(21) Appl. No.: 15/556,746

(22) PCT Filed: Mar. 11, 2016

(86) PCT No.: PCT/US2016/022072
§ 371 (c)(1),
(2) Date: Sep. 8, 2017

(87) PCT Pub. No.: WO2016/145345
PCT Pub. Date: Sep. 15, 2016

(65) Prior Publication Data
US 2018/0043035 A1    Feb. 15, 2018

Related U.S. Application Data

(60) Provisional application No. 62/131,661, filed on Mar. 11, 2015.

(51) Int. Cl.
| | | |
|---|---|---|
| *A61K 38/17* | (2006.01) | |
| *A61K 38/43* | (2006.01) | |
| *C07K 14/00* | (2006.01) | |
| *C07K 14/435* | (2006.01) | |
| *C12N 15/86* | (2006.01) | |
| *A61K 48/00* | (2006.01) | |
| *C07K 14/47* | (2006.01) | |

(52) U.S. Cl.
CPC ........ *A61K 48/005* (2013.01); *A61K 38/1709* (2013.01); *C07K 14/4706* (2013.01); *C12N 15/86* (2013.01); *C12N 2750/14143* (2013.01); *C12N 2830/001* (2013.01); *C12N 2830/008* (2013.01); *C12N 2830/42* (2013.01); *C12N 2830/50* (2013.01)

(58) Field of Classification Search
CPC .... A61K 38/17; A61K 38/1709; A61K 38/43; A61K 48/005; A61K 48/0058; A61K 48/0066; C07K 14/00; C07K 14/435; C12N 15/86; C12N 15/8645; C12N 2750/14143; C12N 2830/00; C12N 2830/008; C12N 2830/42; C12N 2830/50
See application file for complete search history.

(56) References Cited

U.S. PATENT DOCUMENTS

| | | | |
|---|---|---|---|
| 9,770,491 B2* | 9/2017 | Beltran | A61K 48/005 |
| 2010/0081707 A1* | 4/2010 | Ali | A61F 9/0017 |
| | | | 514/44 R |
| 2011/0229971 A1 | 9/2011 | Knop et al. | |
| 2017/0096683 A1* | 4/2017 | Scaria | A61K 48/0075 |

FOREIGN PATENT DOCUMENTS

| | | |
|---|---|---|
| JP | 2001-500014 A | 1/2001 |
| JP | 2014-517694 A | 7/2014 |
| WO | WO 98/10086 A1 | 3/1998 |
| WO | WO 2012/162705 A2 | 11/2012 |
| WO | WO 2014/011210 A1 | 1/2014 |
| WO | WO 14/127196 * | 8/2014 |
| WO | WO 14/140051 * | 9/2014 |
| WO | WO 2015/160893 A1 | 10/2015 |
| WO | WO 2016/001693 A1 | 1/2016 |
| WO | WO 2016/014353 A1 | 1/2016 |
| WO | WO 16/139321 * | 9/2016 |
| WO | WO 2016/145345 A1 | 9/2016 |

OTHER PUBLICATIONS

Wu et al, Mol. Ther. 21(9): Abstract 709, e20, available Sep. 2013.*
Kaneshiro et al, IOVS 52(491): ARVO Annual Meeting Abstract, Apr. 2011.*
Dandekar et al, Br. J. Opthalmol. 88:528-532, 2004.*
Pauer et al, IOVS 55: 6338, ARVO Annual Meeting Abstract, Apr. 2014.*
Veltel et al, Expert Opin. Ther. Targets 13(10):1239-1251, 2009.*
Boye et al, Human Gene Therapy 23:1101-1115, 2012.*
Australian Patent Office, International Search Report issued in PCT/US2016/022072, dated Apr. 28, 2016, 9 pages.
Australian Patent Office, International Preliminary Report on Patentability issued in PCT/US2016/022072, dated Sep. 21, 2017, 13 pages.
Australian Patent Office, Written Opinion of the International Searching Authority issued in PCT/US2016/022072, dated Apr. 28, 2016, 11 pages.

(Continued)

*Primary Examiner* — Kevin K Hill
(74) *Attorney, Agent, or Firm* — Leydig, Voit & Mayer, Ltd.

(57) ABSTRACT

Disclosed are adeno-associated virus (AAV) vectors comprising a nucleotide sequence encoding RP2 or RPGR-ORF15 and related pharmaceutical compositions. Also disclosed are methods of treating or preventing X-linked retinitis pigmentosa, increasing photoreceptor number in a retina of a mammal, and increasing visual acuity of a mammal using the vectors and pharmaceutical compositions.

25 Claims, No Drawings
Specification includes a Sequence Listing.

(56) References Cited

OTHER PUBLICATIONS

Beltran W. et al., "Gene therapy rescues photoreceptor blindness in dogs and paves the way for treating human X-linked retinitis pigmentosa", *PNAS*, (Feb. 2012), vol. 109, No. 6, pp. 2132-2137 and Supporting Information, pp. 1-7, 10.1073/pnas.1118847109 "SI Materials and Methods".
Douglas RM. et al., "Independent visual threshold measurements in the two eyes of freely moving rats and mice using a virtual-reality optokinetic system", *Vis. Neurosci.*, 22: 677-684 (Sep. 2005).
Ghosh AK. et al., "Human retinopathy-associated ciliary protein retinitis pigmentosa GTPase regulator mediates cilia-dependent vertebrate development", *Hum. Mol. Gen.*, 19(1); 90-98 (2010).
Glaus E. et al., "Gene Therapeutic Approach Using Mutation-adapted U1 snRNA to Correct a RPGR Splice Defect in Patient-derived Cells", *Mol. Ther.*, vol. 19, No. 5, 936-941 (May 2011).
Grimm D. et al., "Preclinical in vivo evaluation of psuedotyped adeno-associated virus vectors for liver gene therapy", *Blood*, 102:2412-2419 (Oct. 2003).
Hong D-H. et al., "A retinitis pigmentosa GTPase regulator (RPGR)-deficient mouse model for X-linked retinitis pigmentosa (RP3)", *PNAS*, 97: 3649-3654 (Mar. 2000).
Hong D-H. et al., "Complex expression pattern of RPGR reveals a role for purine-rich exonic splicing enhancers", *Invest. Ophthalmol. Vis. Sci.*, 43: 3373-3382 (Nov. 2002).
Hong D-H. et al., "RPGR isoforms in photoreceptor connecting cilia and the transitional zone of motile cilia", *Invest. Ophthalmol. Vis. Sci.*, 44(6): 2413-2421 (Jun. 2003).
Hong D-H. et al., "A Single, Abbreviated RPGR-ORF15 Varient Reconstitutes RPGR Function In Vivo", *Invest. Ophthalmol. Vis. Sci.*, 46(2): 435-441 (Feb. 2005).
Khani SC. et al., "Aav-mediated expression targeting of rod and cone photoreceptors with a human rhodopsin kinase promoter", *Invest. Ophthalmol. Vis. Sci.*, 48(9): 3954-3961 (Sep. 2007).
Lewin A. et al., "Aav-mediated gene therapy in animal models of autosomal dominant and X-linked retinitis pigmentosa", *Molecular Syndromology*, (2011), vol. 2, No. 6, p. 265, abstract A005_2012.
Li, L. et al., "Ablation of the X-linked retinitis pigmentosa 2 (Rp2) gene in mice results in opsin mislocalization and photoreceptor degeneration", *Invest. Ophthalmol. Vis. Sci.*, 54(7): 4503-4511 (Jul. 2013).
McCarty DM. et al., "Self-complementary AAV Vectors; Advances and Applications", *Mol. Ther.*, vol. 16, No. 10, 1648-1656 (Oct. 2008).
Mookherjee S. et al., "A Long-Term Study of AAV Vector-Mediated Gene Therapy for X-linked Retinitis Pigmentosa (XLRP) Due to RP2 Mutation", *Molecular Therapy*, 2014, vol. 22, Supplement 1, Abstract (published Apr. 26, 2014 and presented May 21, 2014).
Mookherjee S. et al., "A Long-Term Study of AAV Vector-Mediated Gene Therapy for X-linked Retinitis Pigmentosa (XLRP) Due to RP2 Mutation", abstract 122 published in *Molecular Therapy*, 2014, vol. 22, Supplement 1, p. S46 (May 2014).
Mookherjee S. et al., "A Long-Term Study of AAV Vector-Mediated Gene Therapy for X-linked Retinitis Pigmentosa (XLRP) Due to RP2 Mutation", abstract 122 poster for the 2014 American Society of Gene and Cell Therapy (ASGCT) meeting (May 21, 2014).
Mookherjee S. et al, "A low dose AAV vector administration preserves cone function in an RP2 knockout mouse model for retinitis pigmentosa," abstract 3310 for the 2014 Association for Research in Vision and Ophthalmology (ARVO) meeting, (May 3, 2014).
Mookherjee S. et al, "A low dose AAV vector administration preserves cone function in an RP2 knockout mouse model for retinitis pigmentosa," abstract 3310 for the 2014 ARVO meeting, published in *Invest. Ophthalmol. Vis. Sci.*, 2014, vol. 55, No. 13 (Apr. 2014).
Mookherjee S. et al., "A Low Dose AAV Vector Administration Preserves Cone Function in an Rp2 Knockout Mouse Model for Retinitis Pigmentosa," poster for the 2014 Association for Research in Vision and Ophthalmology (ARVO) meeting, (May 3, 2014).
Mookherjee et al., "Adeno-Associated Viral (AAV) Vector-Mediated Gene Therapy for X-linked Retinitis Pigmentosa (XLRP): A Long-Term Efficacy Study in Mouse Models of RPGR or RP2 Deficiency," poster and abstract presented at the NIH Research Festival (Sep. 22, 2014).
Mookherjee et al., "Gene therapy for X-linked retinitis pigmentosa in a knockout mouse model of RP2," abstract for the 2012 American Society of Human Genetics (ASHG) meeting (2012).
Mookherjee S. et al., "Gene Therapy Rescues Cone Function and Viability in an Rp2 Knockout Mouse Model for X-linked Retinitis Pigmentosa Over a Wide Dose Range and a Broad Therapeutic Time Window," *Mol. Ther.*, vol. 23, Supplement 1, abstract 714 (May 2015).
Mookherjee S. et al., "Long-term rescue of cone photoreceptor degeneration in retinitis pigmentosa 2 (RP2)-knockout mice by gene replacement therapy", *Human Molecular Genetics*, 2015 (Epub date Sep. 10, 2015), vol. 24, No. 22, pp. 6446-6458.
Pawlyk B. et al., "Photoreceptor Rescue by an Abbreviated Human RPGR Gene in a Murine Model of X-linked Retinitis Pigmentosa," *Gene Therapy*, (Feb. 2016) (Epub date Oct. 8, 2015), vol. 23(2), pp. 196-204 (author manuscript).
Petrs-Silva et al., "Advances in gene therapy technologies to treat retinitis pigmentosa", *Clin. Ophthalmol.*, 8: 127-136 (2014) (e-published Dec. 24, 2013).
Prusky GT. et al., "Rapid Quantification of Adult and Developing Mouse Spatial Vision Using a Virtual Optomotor System," *Invest. Ophthalmol. Vis. Sci.*, 45(12): 4611-4616 (Dec. 2004).
Shu et al., "Zebrafish Rpgr is required for normal retinal development and plays a role in dynein-based retrograde transport processes," *Hum. Mol. Gen.*, 19(4): 657-670 (2010).
Sun X. et al., "Gene Therapy with a Promoter Targeting Both Rods and Cones Rescues Retinal Degeneration Caused by AIPL1 Mutations," *Gene Therapy*, 17(1): 117-131 (Jan. 2010) (author manuscript).
Vandenberghe LH. et al., "AAV9 Targets Cone Photoreceptors in the Nonhuman Primate Retina," *PLOS One*, 8(1): e53463 (Jan. 2013).
Veltel S. et al., "RPGR and RP2: targets for the treatment of X-linked retinitis pigmentosa?," *Expert Opin. Ther. Targets*, (Oct. 2009), vol. 13, No. 10, pp. 1239-1251.
Wu Z. et al., "Gene therapy for X-linked retinitis pigmentosa: A long-term efficacy study in a mouse model of RPGR deficiency," *Molecular Therapy*, 2014, vol. 22, Supplement 1, abstract 537 (published Apr. 26, 2014 and presented May 23, 2014).
Wu Z. et al., "Gene Therapy for X-Linked Retinitis Pigmentosa: A Long-Term Efficacy Study in a Mouse Model of RPGR Deficiency," presentation given at the 2014 ASGCT meeting (presented May 23, 2014).
Wu Z. et al., "Preclinical development of an AAV vector for the treatment of X-linked retinitis pigmentosa due to RPGRorfl5 mutation," Molecular Therapy, (Sep. 2013), vol. 21, No. 9, abstract 709.
Wu Z. et al., "Preclinical development of AAV vectors for the treatment of X-linked retinitis pigmentosa caused by RPGR mutations," *Invest. Ophthalmol. Vis. Sci* 2014, vol. 55, No. 13, abstract 3305 (Mar. 13, 2014).
Wu Z. et al., "Preclinical development of AAV vectors for the treatment of X-linked retinitis pigmentosa caused by RPGR mutations," poster for the 2014 ARVO meeting (May 3, 2014).
Wu Z. et al., "A long-term efficacy study of gene replacement therapy for RPGR-associated retinal degeneration" *Human Molecular Genetics*, 2015, vol. 24, No. 14: 3956-3970.
Zhang H. et al., "Mistrafficking of prenylated proteins causes retinitis pigmentosa 2", *FASEB J.*, 29(3):932-42. doi: 10.1096/fj.14-257915. (Epub Nov. 24, 2014).
Strausberg et al., Database Gen Bank, [online], Accession No. AAH43348, <https://www.ncbi.nlm.nih.gov/protein/AAH43348>, Jul. 15, 2006, 2 pages.
Japanese Patent Office, Office Action dated Jan. 7, 2020, in Application No. 2017-547425, with English translation, 14 pages.

* cited by examiner

SEQUENCE LISTING

```
<160> NUMBER OF SEQ ID NOS: 27

<210> SEQ ID NO 1
<211> LENGTH: 1053
<212> TYPE: DNA
<213> ORGANISM: Artificial Sequence
<220> FEATURE:
<223> OTHER INFORMATION: Synthetic

<400> SEQUENCE: 1
atgggctgct tcttctccaa gagacggaag gctgacaagg agtcgcggcc cgagaacgag        60
gaggagcggc caaagcagta cagctgggat cagcgcgaga aggttgatcc aaaagactac       120
atgttcagtg gactgaagga tgaaacagta ggtcgcttac ctgggacggt agcaggacaa       180
cagtttctca ttcaagactg tgagaactgt aacatctata tttttgatca ctctgctaca       240
gttaccattg atgactgtac taactgcata attttctgg gacccgtgaa aggcagcgtg        300
tttttccgga attgcagaga ttgcaagtgc acattagcct gccaacaatt tcgtgtgcga       360
gattgtagaa agctggaagt cttttttgtgt tgtgccactc aacccatcat tgagtcttcc      420
tcaaatatca aatttggatg ttttcaatgg tactatcctg aattagcttt ccagttcaaa       480
gatgcagggc taagtatctt caacaataca tggagtaaca ttcatgactt tacacctgtg      540
tcaggagaac tcaactggag ccttcttcca gaagatgctg tggttcagga ctatgttcct      600
atacctacta ccgaagagct caaagctgtt cgtgtttcca cagaagccaa tagaagcatt      660
gttccaatat cccggggtca gagacagaag agcagcgatg aatcatgctt agtggtatta      720
tttgctggtg attacactat tgcaaatgcc agaaaactaa ttgatgagat ggttggtaaa      780 ggcttttttcc tagttcagac aaaggaagtg tccatgaaag ctgaggatgc tcaaagggtt      840
tttcgggaaa aagcacctga cttccttcct cttctgaaca aaggtcctgt tattgccttg      900
gagtttaatg gggatggtgc tgtagaagta tgtcaactta ttgtaaacga gatattcaat       960
gggaccaaga tgtttgtatc tgaaagcaag gagacggcat ctggagatgt agacagcttc     1020
tacaactttg ctgatataca gatgggaata tga                                   1053

<210> SEQ ID NO 2
<211> LENGTH: 350
<212> TYPE: PRT
<213> ORGANISM: Homo sapiens

<400> SEQUENCE: 2

Met Gly Cys Phe Phe Ser Lys Arg Arg Lys Ala Asp Lys Glu Ser Arg
1               5                   10                  15
```

```
Pro Glu Asn Glu Glu Arg Pro Lys Gln Tyr Ser Trp Asp Gln Arg
            20                  25                  30

Glu Lys Val Asp Pro Lys Asp Tyr Met Phe Ser Gly Leu Lys Asp Glu
        35                  40                  45

Thr Val Gly Arg Leu Pro Gly Thr Val Ala Gly Gln Gln Phe Leu Ile
 50                  55                  60

Gln Asp Cys Glu Asn Cys Asn Ile Tyr Ile Phe Asp His Ser Ala Thr
65                  70                  75                  80

Val Thr Ile Asp Asp Cys Thr Asn Cys Ile Ile Phe Leu Gly Pro Val
                85                  90                  95

Lys Gly Ser Val Phe Phe Arg Asn Cys Arg Asp Cys Lys Cys Thr Leu
            100                 105                 110

Ala Cys Gln Gln Phe Arg Val Arg Asp Cys Arg Lys Leu Glu Val Phe
        115                 120                 125

Leu Cys Cys Ala Thr Gln Pro Ile Ile Glu Ser Ser Ser Asn Ile Lys
130                 135                 140

Phe Gly Cys Phe Gln Trp Tyr Tyr Pro Glu Leu Ala Phe Gln Phe Lys
145                 150                 155                 160

Asp Ala Gly Leu Ser Ile Phe Asn Asn Thr Trp Ser Asn Ile His Asp
                165                 170                 175

Phe Thr Pro Val Ser Gly Glu Leu Asn Trp Ser Leu Leu Pro Glu Asp
            180                 185                 190

Ala Val Val Gln Asp Tyr Val Pro Ile Pro Thr Thr Glu Glu Leu Lys
        195                 200                 205

Ala Val Arg Val Ser Thr Glu Ala Asn Arg Ser Ile Val Pro Ile Ser
210                 215                 220

Arg Gly Gln Arg Gln Lys Ser Ser Asp Glu Ser Cys Leu Val Val Leu
225                 230                 235                 240

Phe Ala Gly Asp Tyr Thr Ile Ala Asn Ala Arg Lys Leu Ile Asp Glu
                245                 250                 255

Met Val Gly Lys Gly Phe Phe Leu Val Gln Thr Lys Glu Val Ser Met
            260                 265                 270

Lys Ala Glu Asp Ala Gln Arg Val Phe Arg Glu Lys Ala Pro Asp Phe
        275                 280                 285

Leu Pro Leu Leu Asn Lys Gly Pro Val Ile Ala Leu Glu Phe Asn Gly
290                 295                 300

Asp Gly Ala Val Glu Val Cys Gln Leu Ile Val Asn Glu Ile Phe Asn
305                 310                 315                 320

Gly Thr Lys Met Phe Val Ser Glu Ser Lys Glu Thr Ala Ser Gly Asp
                325                 330                 335

Val Asp Ser Phe Tyr Asn Phe Ala Asp Ile Gln Met Gly Ile
            340                 345                 350

<210> SEQ ID NO 3
<211> LENGTH: 3459
<212> TYPE: DNA
<213> ORGANISM: Artificial Sequence
<220> FEATURE:
<223> OTHER INFORMATION: Synthetic

<400> SEQUENCE: 3
atgagggagc cggaagagct gatgcccgat tcgggtgctg tgtttacatt tgggaaaagt      60
aaatttgctg aaaataatcc cggtaaattc tggtttaaaa atgatgtccc tgtacatctt     120
tcatgtggag atgaacattc tgctgttgtt accggaaata ataaacttta catgtttggc     180
```

```
agtaacaact ggggtcagtt aggattagga tcaaagtcag ccatcagcaa gccaacatgt    240
gtcaaagctc taaaacctga aaaagtgaaa ttagctgcct gtggaaggaa ccacaccctg    300
gtgtcaacag aaggaggcaa tgtatatgca actggtggaa ataatgaagg acagttgggg    360
cttggtgaca ccgaagaaag aaacactttt catgtaatta gcttttttac atccgagcat    420
aagattaagc agctgtctgc tggatctaat acttcagctg ccctaactga ggatggaaga    480 cttttatgt ggggtgacaa ttccgaaggg caaattggtt taaaaaatgt aagtaatgtc    540
tgtgtccctc agcaagtgac cattgggaaa cctgtctcct ggatctcttg tggatattac    600
cattcagctt ttgtaacaac agatggtgag ctatatgtgt ttggagaacc tgagaatggg    660
aagttaggtc ttcccaatca gctcctgggc aatcacagaa caccccagct ggtgtctgaa    720
attccggaga aggtgatcca agtagcctgt ggtggagagc atactgtggt tctcacggag    780
aatgctgtgt atacctttgg gctgggacaa tttggtcagc tgggtcttgg cacttttctt    840
tttgaaactt cagaacccaa agtcattgag aatattaggg atcaaacaat aagttatatt    900
tcttgtggag aaaatcacac agctttgata acagatatcg gccttatgta acttttgga    960 gatggtcgcc acggaaaatt aggacttgga ctggagaatt ttaccaatca cttcattcct   1020
actttgtgct ctaattttt gaggtttata gttaaattgg ttgcttgtgg tggatgtcac   1080
atggtagttt ttgctgctcc tcatcgtggt gtggcaaaag aaattgaatt cgatgaaata   1140
aatgatactt gcttatctgt ggcgactttt ctgccgtata gcagtttaac ctcaggaaat   1200
gtactgcaga ggactctatc agcacgtatg cggcgaagag agaggagag gtctccagat   1260 tcttttcaa tgaggagaac actacctcca atagaaggga ctcttggcct ttctgcttgt   1320
tttctcccca attcagtctt tccacgatgt tctgagagaa acctccaaga gagtgtctta   1380
tctgaacagg acctcatgca gccagaggaa ccagattatt tgctagatga aatgaccaaa   1440
gaagcagaga tagataattc ttcaactgta gaaagccttg gagaaactac tgatatctta   1500
aacatgacac acatcatgag cctgaattcc aatgaaaagt cattaaaatt atcaccagtt   1560
cagaaacaaa agaaacaaca aacaattggg gaactgacgc aggatacagc tcttactgaa   1620
aacgatgata gtgatgaata tgaagaaatg tcagaaatga agaagggaa agcatgtaaa   1680 caacatgtgt cacaagggat tttcatgacg cagccagcta cgactatcga agcattttca   1740
gatgaggaag tagagatccc agaggagaag gaaggagcag aggattcaaa aggaaatgga   1800
atagaggagc aagaggtaga agcaaatgag gaaaatgtga aggtgcatgg aggaagaaag   1860
gagaaaacag agatcctatc agatgacctt acagacaaag cagaggtgag tgaaggcaag   1920
gcaaaatcag tgggagaagc agaggatggg cctgaaggta gagggatgg aacctgtgag   1980 gaaggtagtt caggagcaga acactggcaa gatgaggaga gggagaaggg ggagaaagac   2040
aagggtagag gagaaatgga gaggccagga gagggagaga aggaactagc agagaaggaa   2100
gaatggaaga agagggatgg ggaagagcag gagcaaaagg agagggagca gggccatcag   2160
aaggaaagaa accaagagat ggaggaggga ggggaggagg agcatggaga aggagaagaa   2220
gaggagggag acagaagga ggaagaagag aaggagggag aagggaaaga ggaaggagaa   2280
ggggaagaag tggagggaga acgtgaaaag gaggaaggag agaggaaaaa ggaggaagaa   2340
gcggggaagg aggagaaagg agaggaagaa ggagaccaag gagaggggga gaggaggaa   2400 acagagggga gaggagagga aaaagaggag ggaggggaag tagagggagg ggaagtagag   2460 gagggaaag gagagaggga agaggaagag gaggagggtg aggggaaga ggaggaaggg   2520
```

```
gaggggggaag aggaggaagg ggaggggggaa gaggaggaag gagaagggaa aggggaggaa     2580 gaagggggaag aaggagaagg ggaggaagaa gggggaggaag gagaaggggga ggggggaagag    2640 gaggaaggag aaggggaggg agaagaggaa ggagaagggg agggagaaga ggaggaagga      2700
gaaggggagg gagaagagga aggggaagag gagggagaag aggaggaagg agaagggaaa      2760
ggggaggagg aaggagagga aggagaaggg gaggggggaag aggaggaagg agaagggggaa    2820 ggggaggatg gagaagggga ggggggaagag gaggaaggag aatgggaggg ggaagaggag     2880
gaaggagaag gggaggggga agaggaagga gaagaggaag ggggaggaagg agaaggggag     2940 ggggaagagg aggaaggaga agggggaggggg gaagaggagg aaggggaaga agaaggggag   3000
gaagaaggag agggagagga agaaggggag ggagaagggg aggaagaaga ggaagggggaa    3060 gtggaagggg aggtggaagg ggaggaagga gaggggggaag gagaggaaga ggaaggagag    3120
gaggaaggag aagaaaggga aaaggaggggg gaaggagaag aaaacaggag gaacagagaa    3180
gaggaggagg aagaagaggg gaagtatcag gagacaggcg aagaagagaa tgaaaggcag     3240
gatggagagg agtacaaaaa agtgagcaaa ataaaaggat ctgtgaaata tggcaaacat     3300
aaaacatatc aaaaaaagtc agttactaac acacagggaa atgggaaaga gcagaggtcc    3360
aaaatgccag tccagtcaaa acgacttttta aaaaacgggc catcaggttc caaaaagttc   3420
tggaataatg tattaccaca ttacttggaa ttgaagtaa                           3459
```

```
<210> SEQ ID NO 4
<211> LENGTH: 1152
<212> TYPE: PRT
<213> ORGANISM: Homo sapiens

<400> SEQUENCE: 4

Met Arg Glu Pro Glu Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
            20                  25                  30

Lys Asn Asp Val Pro Val His Leu Ser Cys Gly Asp Glu His Ser Ala
        35                  40                  45

Val Val Thr Gly Asn Asn Lys Leu Tyr Met Phe Gly Ser Asn Asn Trp
    50                  55                  60

Gly Gln Leu Gly Leu Gly Ser Lys Ser Ala Ile Ser Lys Pro Thr Cys
65                  70                  75                  80

Val Lys Ala Leu Lys Pro Glu Lys Val Lys Leu Ala Ala Cys Gly Arg
                85                  90                  95

Asn His Thr Leu Val Ser Thr Glu Gly Gly Asn Val Tyr Ala Thr Gly
            100                 105                 110

Gly Asn Asn Glu Gly Gln Leu Gly Leu Gly Asp Thr Glu Glu Arg Asn
        115                 120                 125

Thr Phe His Val Ile Ser Phe Phe Thr Ser Glu His Lys Ile Lys Gln
    130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
            180                 185                 190

Ser Trp Ile Ser Cys Gly Tyr Tyr His Ser Ala Phe Val Thr Thr Asp
        195                 200                 205
```

-continued

Gly Glu Leu Tyr Val Phe Gly Glu Pro Glu Asn Gly Lys Leu Gly Leu
         210                 215                 220

Pro Asn Gln Leu Leu Gly Asn His Arg Thr Pro Gln Leu Val Ser Glu
225                 230                 235                 240

Ile Pro Glu Lys Val Ile Gln Val Ala Cys Gly Gly Glu His Thr Val
                245                 250                 255

Val Leu Thr Glu Asn Ala Val Tyr Thr Phe Gly Leu Gly Gln Phe Gly
         260                 265                 270

Gln Leu Gly Leu Gly Thr Phe Leu Phe Glu Thr Ser Glu Pro Lys Val
         275                 280                 285

Ile Glu Asn Ile Arg Asp Gln Thr Ile Ser Tyr Ile Ser Cys Gly Glu
290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335

His Phe Ile Pro Thr Leu Cys Ser Asn Phe Leu Arg Phe Ile Val Lys
                340                 345                 350

Leu Val Ala Cys Gly Gly Cys His Met Val Val Phe Ala Ala Pro His
         355                 360                 365

Arg Gly Val Ala Lys Glu Ile Glu Phe Asp Glu Ile Asn Asp Thr Cys
         370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Arg Glu Arg Glu
                405                 410                 415

Arg Ser Pro Asp Ser Phe Ser Met Arg Arg Thr Leu Pro Pro Ile Glu
                420                 425                 430

Gly Thr Leu Gly Leu Ser Ala Cys Phe Leu Pro Asn Ser Val Phe Pro
         435                 440                 445

Arg Cys Ser Glu Arg Asn Leu Gln Glu Ser Val Leu Ser Glu Gln Asp
         450                 455                 460

Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
                485                 490                 495

Thr Asp Ile Leu Asn Met Thr His Ile Met Ser Leu Asn Ser Asn Glu
                500                 505                 510

Lys Ser Leu Lys Leu Ser Pro Val Gln Lys Gln Lys Gln Gln Thr
         515                 520                 525

Ile Gly Glu Leu Thr Gln Asp Thr Ala Leu Thr Glu Asn Asp Asp Ser
         530                 535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
                565                 570                 575

Glu Ala Phe Ser Asp Glu Glu Val Glu Ile Pro Glu Glu Lys Glu Gly
                580                 585                 590

Ala Glu Asp Ser Lys Gly Asn Gly Ile Glu Glu Gln Val Glu Ala
         595                 600                 605

Asn Glu Glu Asn Val Lys Val His Gly Gly Arg Lys Glu Lys Thr Glu
610                 615                 620

Ile Leu Ser Asp Asp Leu Thr Asp Lys Ala Glu Val Ser Glu Gly Lys

-continued

```
            625                 630                 635                 640
Ala Lys Ser Val Gly Glu Ala Glu Asp Gly Pro Glu Gly Arg Gly Asp
                        645                 650                 655

Gly Thr Cys Glu Glu Gly Ser Ser Gly Ala Glu His Trp Gln Asp Glu
                660                 665                 670

Glu Arg Glu Lys Gly Glu Lys Asp Lys Gly Arg Gly Glu Met Glu Arg
            675                 680                 685

Pro Gly Glu Gly Glu Lys Glu Leu Ala Glu Lys Glu Glu Trp Lys Lys
        690                 695                 700

Arg Asp Gly Glu Glu Gln Glu Gln Lys Glu Arg Glu Gln Gly His Gln
705                 710                 715                 720

Lys Glu Arg Asn Gln Glu Met Glu Glu Gly Glu Glu Glu His Gly
                725                 730                 735

Glu Gly Glu Glu Glu Gly Asp Arg Glu Glu Glu Glu Glu Lys Glu
                740                 745                 750

Gly Glu Gly Lys Glu Gly Glu Gly Glu Val Glu Gly Glu Arg
                755                 760                 765

Glu Lys Glu Glu Gly Glu Arg Lys Lys Glu Glu Arg Ala Gly Lys Glu
    770                 775                 780

Glu Lys Gly Glu Glu Glu Gly Asp Gln Gly Glu Gly Glu Glu Glu
785                 790                 795                 800

Thr Glu Gly Arg Gly Glu Glu Lys Glu Glu Gly Gly Glu Val Glu Gly
                805                 810                 815

Gly Glu Val Glu Glu Gly Lys Gly Glu Arg Glu Glu Glu Glu Glu
                820                 825                 830

Gly Glu Gly Glu Glu Glu Gly Glu Gly Glu Glu Glu Glu Gly Glu
                835                 840                 845

Gly Glu Glu Glu Glu Gly Glu Lys Gly Glu Glu Glu Gly Glu Glu
    850                 855                 860

Gly Glu Gly Glu Glu Glu Glu Gly Glu Glu Gly Glu Gly Glu Glu
865                 870                 875                 880

Glu Glu Gly Glu Gly Glu Gly Glu Glu Gly Glu Gly Glu Gly Glu
                885                 890                 895

Glu Glu Glu Gly Glu Gly Glu Gly Glu Glu Gly Glu Gly Glu Gly
                900                 905                 910

Glu Glu Glu Glu Gly Glu Gly Lys Gly Glu Glu Gly Glu Glu Gly
            915                 920                 925

Glu Gly Glu Gly Glu Glu Glu Gly Glu Gly Glu Gly Glu Asp Gly
        930                 935                 940

Glu Gly Glu Gly Glu Gly Glu Gly Glu Trp Glu Gly Glu Glu Glu
945                 950                 955                 960

Glu Gly Glu Gly Glu Gly Glu Gly Glu Gly Glu Gly Glu Glu Glu
                965                 970                 975

Gly Glu Gly Glu Gly Glu Glu Glu Gly Glu Gly Glu Gly Glu Glu
                980                 985                 990

Glu Glu Gly Glu Glu Glu Gly Glu  Glu Glu Gly Glu Gly  Glu Glu Glu
            995                 1000                1005

Gly Glu  Gly Glu Gly Glu Glu  Glu Glu Glu Gly Glu  Val Glu Gly
        1010                1015                1020

Glu Val  Glu Gly Glu Glu Gly  Glu Gly Glu Gly Glu  Glu Glu Glu
        1025                1030                1035

Gly Glu  Glu Glu Gly Glu Glu  Arg Glu Lys Glu Gly  Glu Gly Glu
        1040                1045                1050
```

-continued

Glu Asn Arg Arg Asn Arg Glu Glu Glu Glu Glu Gly Lys
    1055            1060                1065

Tyr Gln Glu Thr Gly Glu Glu Asn Glu Arg Gln Asp Gly Glu
    1070            1075                1080

Glu Tyr Lys Lys Val Ser Lys Ile Lys Gly Ser Val Lys Tyr Gly
    1085            1090                1095

Lys His Lys Thr Tyr Gln Lys Lys Ser Val Thr Asn Thr Gln Gly
    1100            1105                1110

Asn Gly Lys Glu Gln Arg Ser Lys Met Pro Val Gln Ser Lys Arg
    1115            1120                1125

Leu Leu Lys Asn Gly Pro Ser Gly Ser Lys Lys Phe Trp Asn Asn
    1130            1135                1140

Val Leu Pro His Tyr Leu Glu Leu Lys
    1145            1150

<210> SEQ ID NO 5
<211> LENGTH: 738
<212> TYPE: PRT
<213> ORGANISM: adeno-associated virus

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp

```
                    260             265             270
Asn Thr Tyr Phe Gly Tyr Ser Thr Pro Trp Gly Tyr Phe Asp Phe Asn
                275             280             285

Arg Phe His Cys His Phe Ser Pro Arg Asp Trp Gln Arg Leu Ile Asn
            290             295             300

Asn Asn Trp Gly Phe Arg Pro Lys Arg Leu Ser Phe Lys Leu Phe Asn
305             310             315             320

Ile Gln Val Lys Glu Val Thr Gln Asn Glu Gly Thr Lys Thr Ile Ala
                325             330             335

Asn Asn Leu Thr Ser Thr Ile Gln Val Phe Thr Asp Ser Glu Tyr Gln
            340             345             350

Leu Pro Tyr Val Leu Gly Ser Ala His Gln Gly Cys Leu Pro Pro Phe
            355             360             365

Pro Ala Asp Val Phe Met Ile Pro Gln Tyr Gly Tyr Leu Thr Leu Asn
            370             375             380

Asn Gly Ser Gln Ala Val Gly Arg Ser Ser Phe Tyr Cys Leu Glu Tyr
385             390             395             400

Phe Pro Ser Gln Met Leu Arg Thr Gly Asn Asn Phe Gln Phe Thr Tyr
                405             410             415

Thr Phe Glu Asp Val Pro Phe His Ser Ser Tyr Ala His Ser Gln Ser
                420             425             430

Leu Asp Arg Leu Met Asn Pro Leu Ile Asp Gln Tyr Leu Tyr Tyr Leu
            435             440             445

Ser Arg Thr Gln Thr Thr Gly Gly Thr Ala Asn Thr Gln Thr Leu Gly
            450             455             460

Phe Ser Gln Gly Gly Pro Asn Thr Met Ala Asn Gln Ala Lys Asn Trp
465             470             475             480

Leu Pro Gly Pro Cys Tyr Arg Gln Gln Arg Val Ser Thr Thr Thr Gly
                485             490             495

Gln Asn Asn Asn Ser Asn Phe Ala Trp Thr Ala Gly Thr Lys Tyr His
            500             505             510

Leu Asn Gly Arg Asn Ser Leu Ala Asn Pro Gly Ile Ala Met Ala Thr
            515             520             525

His Lys Asp Asp Glu Glu Arg Phe Phe Pro Ser Asn Gly Ile Leu Ile
            530             535             540

Phe Gly Lys Gln Asn Ala Ala Arg Asp Asn Ala Asp Tyr Ser Asp Val
545             550             555             560

Met Leu Thr Ser Glu Glu Glu Ile Lys Thr Thr Asn Pro Val Ala Thr
                565             570             575

Glu Glu Tyr Gly Ile Val Ala Asp Asn Leu Gln Gln Gln Asn Thr Ala
            580             585             590

Pro Gln Ile Gly Thr Val Asn Ser Gln Gly Ala Leu Pro Gly Met Val
            595             600             605

Trp Gln Asn Arg Asp Val Tyr Leu Gln Gly Pro Ile Trp Ala Lys Ile
            610             615             620

Pro His Thr Asp Gly Asn Phe His Pro Ser Pro Leu Met Gly Gly Phe
625             630             635             640

Gly Leu Lys His Pro Pro Pro Gln Ile Leu Ile Lys Asn Thr Pro Val
                645             650             655

Pro Ala Asp Pro Pro Thr Thr Phe Asn Gln Ser Lys Leu Asn Ser Phe
            660             665             670

Ile Thr Gln Tyr Ser Thr Gly Gln Val Ser Val Glu Ile Glu Trp Glu
            675             680             685
```

Leu Gln Lys Glu Asn Ser Lys Arg Trp Asn Pro Glu Ile Gln Tyr Thr
        690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 6
<211> LENGTH: 210
<212> TYPE: DNA
<213> ORGANISM: Artificial Sequence
<220> FEATURE:
<223> OTHER INFORMATION: Synthetic

<400> SEQUENCE: 6
ctcgctttct tgctgtccaa tttctattaa aggttccttt gttccctaag tccaactact      60
aaactggggg atattatgaa gggccttgag catctggatt ctgcctaata aaaacattt     120 attttcattg caatgatgta tttaaattat ttctgaatat tttactaaaa agggaatgtg    180
ggaggtcagt gcatttaaaa cataaagaaa                                     210

<210> SEQ ID NO 7
<211> LENGTH: 114
<212> TYPE: DNA
<213> ORGANISM: Artificial Sequence
<220> FEATURE:
<223> OTHER INFORMATION: Synthetic

<400> SEQUENCE: 7
gattctgcct aataaaaaac atttattttc attgcaatga tgtatttaaa ttatttctga     60 atatttact aaaaagggaa tgtgggaggt cagtgcattt aaaacataaa gaaa           114

<210> SEQ ID NO 8
<211> LENGTH: 220
<212> TYPE: DNA
<213> ORGANISM: Artificial Sequence
<220> FEATURE:
<223> OTHER INFORMATION: Synthetic

<400> SEQUENCE: 8
gtgcattgga acgcggattc cccgtgccaa gagtgacgta agtaccgcct atagagtcta     60
taggcccacc cccttgcttt tattttttgg ttgggataag ctggattat tctgagtcca    120 agctaggccc ttttgctaat catcttcata cctcttatct tcctcccaca gctcctgggc   180
aacgtgctgg tctgtgtgct ggcccatcac tttggcaaag                          220

<210> SEQ ID NO 9
<211> LENGTH: 285
<212> TYPE: DNA
<213> ORGANISM: Artificial Sequence
<220> FEATURE:
<223> OTHER INFORMATION: Synthetic

<400> SEQUENCE: 9
gtgcattgga acgcggattc cccgtgccaa gagtgacgta agtaccgcct atagagtcta     60
taggcccacc cccttggctt cttatgcatg ctatactgtt ttcatattgc taatagcagc    120
tacaatccag ctaccattct gcttttattt tatggttggg ataaggctgg attattctga   180
gtccaagcta ggcccttttg ctaatcatgt tcatacctct tatcttcctc ccacagctcc   240
tgggcaacgt gctggtctgt gtgctggccc atcactttgg caaag        285

<210> SEQ ID NO 10
<211> LENGTH: 295
<212> TYPE: DNA
<213> ORGANISM: Artificial Sequence
<220> FEATURE:
<223> OTHER INFORMATION: Synthetic

<400> SEQUENCE: 10
gggccccaga agcctggtgg ttgtttgtcc ttctcagggg aaaagtgagg cggccccttg        60
gaggaagggg ccgggcagaa tgatctaatc ggattccaag cagctcaggg gattgtcttt        120
ttctagcacc ttcttgccac tcctaagcgt cctccgtgac cccggctggg atttagcctg        180
gtgctgtgtc agccccgggc tcccagggc ttcccagtgg tccccaggaa ccctcgacag        240
ggccagggcg tctctctcgt ccagcaaggg cagggacggg ccacaggcca agggc            295

<210> SEQ ID NO 11
<211> LENGTH: 130
<212> TYPE: DNA
<213> ORGANISM: Artificial Sequence
<220> FEATURE:
<223> OTHER INFORMATION: Synthetic

<400> SEQUENCE: 11
ctgcgcgctc gctcgctcac tgaggccgcc cgggcaaagc ccgggcgtcg ggcgaccttt        60
ggtcgcccgg cctcagtgag cgagcgagcg cgcagagagg gagtggccaa ctccatcact        120
aggggttcct                                                              130

<210> SEQ ID NO 12
<211> LENGTH: 145
<212> TYPE: DNA
<213> ORGANISM: Artificial Sequence
<220> FEATURE:
<223> OTHER INFORMATION: Synthetic

<400> SEQUENCE: 12
aggaacccct agtgatggag ttggccactc cctctctgcg cgctcgctcg ctcactgagg        60
ccgcccgggc aaagcccggg cgtcgggcga ccttttggtcg cccggcctca gtgagcgagc        120
gagcgcgcag agggagtg gccaa                                               145

<210> SEQ ID NO 13
<211> LENGTH: 106
<212> TYPE: DNA
<213> ORGANISM: Artificial Sequence
<220> FEATURE:
<223> OTHER INFORMATION: Synthetic

<400> SEQUENCE: 13
ctgcgcgctc gctcgctcac tgaggccgcc cgggcaaagc ccgggcgtcg ggcgaccttt        60
ggtcgcccgg cctcagtgag cgagcgagcg cgcagagagg gagtgg                      106

<210> SEQ ID NO 14
<211> LENGTH: 2087
<212> TYPE: DNA
<213> ORGANISM: Artificial Sequence
<220> FEATURE:
<223> OTHER INFORMATION: Synthetic

<400> SEQUENCE: 14

```
ctgcgcgctc gctcgctcac tgaggccgcc cgggcaaagc ccgggcgtcg ggcgaccttt         60
ggtcgcccgg cctcagtgag cgagcgagcg cgcagagagg gagtgggggg gatccactag        120
ttctagagcg gccgctgggc cccagaagcc tggtggttgt ttgtccttct caggggaaaa        180
gtgaggcggc cccttggagg aaggggccgg gcagaatgat ctaatcggat tccaagcagc        240 tcagggggatt gtcttttcct agcaccttct tgccactcct aagcgtcctc cgtgaccccg        300
gctgggattt agcctggtgc tgtgtcagcc ccgggctccc aggggcttcc cagtggtccc        360
caggaaccct cgacagggcc agggcgtctc tctcgtccag caagggcagg gacgggccac        420
aggccaaggg ccgcggccgg gaacggtgca ttggaacgcg gattcccgt gccaagagtg         480 acgtaagtac cgcctataga gtctataggc ccaccccctt ggcttcttat gcatgctata       540 ctgtttttcat attgctaata gcagctacaa tccagctacc attctgcttt tattttatgg      600
ttgggataag gctggattat tctgagtcca agctaggccc ttttgctaat catgttcata       660
cctcttatct tcctcccaca gctcctgggc aacgtgctgg tctgtgtgct ggcccatcac       720
tttggcaaag aattgggatt cgaacatcga tagccaccat gggctgcttc ttctccaaga       780
gacggaaggc tgacaaggag tcgcggcccg agaacgagga ggagcggcca aagcagtaca       840
gctgggatca gcgcgagaag gttgatccaa aagactacat gttcagtgga ctgaaggatg      900
aaacagtagg tcgcttacct gggacggtag caggacaaca gtttctcatt caagactgtg      960
agaactgtaa catctatatt tttgatcact ctgctacagt taccattgat gactgtacta     1020
actgcataat ttttctggga cccgtgaaag gcagcgtgtt tttccggaat gcagagatt      1080 gcaagtgcac attagcctgc caacaatttc gtgtgcgaga ttgtagaaag ctggaagtct    1140
ttttgtgttg tgccactcaa cccatcattg agtcttcctc aaatatcaaa tttggatgtt     1200
ttcaatggta ctatcctgaa ttagctttcc agttcaaaga tgcagggcta agtatcttca    1260
acaatacatg gagtaacatt catgacttta cacctgtgtc aggagaactc aactggagcc    1320
ttcttccaga agatgctgtg gttcaggact atgttcctat acctactacc gaagagctca    1380
aagctgttcg tgtttccaca gaagccaata gaagcattgt tccaatatcc cggggtcaga    1440
gacagaagag cagcgatgaa tcatgcttag tggtattatt tgctggtgat tacactattg    1500
caaatgccag aaaactaatt gatgagatgg ttggtaaagg cttttttccta gttcagacaa   1560 aggaagtgtc catgaaagct gaggatgctc aaagggttttt tcgggaaaaa gcacctgact   1620
tccttcctct tctgaacaaa ggtcctgtta ttgccttgga gtttaatggg gatggtgctg    1680
tagaagtatg tcaacttatt gtaaacgaga tattcaatgg gaccaagatg tttgtatctg    1740 aaaagcaagga gacggcatct ggagatgtag acagcttcta caactttgct gatatacaga   1800
tgggaatatg actcgagatt ctgcctaata aaaacatttt atttttcattg caatgatgta   1860 tttaaattat ttctgaatat tttactaaaa agggaatgtg ggaggtcagt gcattttaaa    1920
cataaagaaa gtagggcgcg ccaggaaccc ctagtgatgg agttggccac tccctctctg    1980
cgcgctcgct cgctcactga ggccgcccgg gcaaagcccg ggcgtcgggc gacctttggt    2040
cgcccggcct cagtgagcga gcgagcgcgc agagagggag tggccaa                   2087
```

<210> SEQ ID NO 15
<211> LENGTH: 4561
<212> TYPE: DNA
<213> ORGANISM: Artificial Sequence
<220> FEATURE:
<223> OTHER INFORMATION: Synthetic

<400> SEQUENCE: 15

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct gcggccgctg gccccagaa gcctggtggt tgtttgtcct tctcagggga    180
aaagtgaggg ggcccttgg aggaaggggc cgggcagaat gatctaatcg gattccaagc    240
agctcagggg attgtctttt tctagcacct tcttgccact cctaagcgtc ctccgtgacc   300
ccggctggga tttagcctgg tgctgtgtca gccccgggct cccaggggct cccagtggt    360
ccccaggaac cctcgacagg gccagggcgt ctctctcgtc cagcaagggc agggacgggc   420
cacaggccaa gggccgcggc cgggaacggt gcattggaac gcggattccc cgtgccaaga   480
gtgacgtaag taccgcctat agagtctata ggcccacccc cttgctttta ttttttggtt   540
gggataaggc tggattattc tgagtccaag ctaggccctt tgctaatca tcttcatacc    600
tcttatcttc ctcccacagc tcctgggcaa cgtgctggtc tgtgtgctgg cccatcactt   660
tggcaaagaa ttatcgatag ccaccatgag ggagccggaa gagctgatgc ccgattcggg   720
tgctgtgttt acatttggga aaagtaaatt tgctgaaaat aatcccggta aattctggtt   780
taaaaatgat gtccctgtac atctttcatg tggagatgaa cattctgctg ttgttaccgg   840
aaataataaa ctttacatgt ttggcagtaa caactggggt cagttaggat taggatcaaa   900
gtcagccatc agcaagccaa catgtgtcaa agctctaaaa cctgaaaaag tgaaattagc   960
tgcctgtgga aggaaccaca ccctggtgtc aacagaagga ggcaatgtat atgcaactgg  1020
tggaaataat gaaggacagt tggggcttgg tgacaccgaa gaagaaaca cttttcatgt   1080
aattagcttt tttacatccg agcataagat taagcagctg tctgctggat ctaatacttc  1140
agctgcccta actgaggatg gaagactttt tatgtggggt gacaattccg aagggcaaat  1200
tggtttaaaa aatgtaagta atgtctgtgt ccctcagcaa gtgaccattg ggaaacctgt   1260
ctcctggatc tcttgtggat attaccattc agcttttgta acaacagatg gtgagctata  1320
tgtgtttgga gaacctgaga atgggaagtt aggtcttccc aatcagctcc tgggcaatca   1380
cagaacaccc cagctggtgt ctgaaattcc ggagaaggtg atccaagtag cctgtggtgg   1440
agagcatact gtggttctca cggagaatgc tgtgtatacc tttgggctgg acaatttgg   1500
tcagctgggt cttggcactt ttcttttga acttcagaa cccaaagtca ttgagaatat    1560
tagggatcaa acaataagtt atatttcttg tggagaaaat cacacagctt tgataacaga   1620
tatcggcctt atgtatactt ttggagatgg tcgccacgga aaattaggac ttggactgga   1680
gaattttacc aatcacttca ttcctacttt tgtgctctaat tttttgaggt ttatagttaa   1740
attggttgct tgtggtggat gtcacatggt agttttgct gctcctcatc gtggtgtggc    1800
aaaagaaatt gaattcgatg aaataaatga tacttgctta tctgtggcga cttttctgcc   1860
gtatagcagt ttaacctcag gaaatgtact gcagaggact ctatcagcac gtatgcggcg   1920
aagagagagg gagaggtctc cagattcttt ttcaatgagg agaacactac ctccaataga   1980
agggactctt ggcctttctg cttgttttct ccccaattca gtctttccac gatgttctga   2040
gagaaacctc caagagagtg tcttatctga acaggacctc atgcagccag aggaaccaga  2100
ttatttgcta gatgaaatga ccaaagaagc agagatagat aattcttcaa ctgtagaaag  2160
ccttggagaa actactgata tcttaaacat gacacacatc atgagcctga attccaatga   2220
aaagtcatta aaattatcac cagttcagaa acaaaagaaa caacaaacaa ttggggaact   2280
gacgcaggat acagctctta ctgaaaacga tgatagtgat gaatatgaag aaatgtcaga   2340
```

```
aatgaaagaa gggaaagcat gtaaacaaca tgtgtcacaa gggattttca tgacgcagcc      2400
agctacgact atcgaagcat tttcagatga ggaagtagag atcccagagg agaaggaagg      2460
agcagaggat tcaaaaggaa atggaataga ggagcaagag gtagaagcaa atgaggaaaa      2520
tgtgaaggtg catggaggaa gaaaggagaa aacagagatc ctatcagatg accttacaga      2580
caaagcagag gtgagtgaag gcaaggcaaa atcagtggga gaagcagagg atgggcctga      2640
aggtagaggg gatggaacct gtgaggaagg tagttcagga gcagaacact ggcaagatga      2700
ggagagggag aagggggaga aagacaaggg tagaggagaa atggagaggc caggagaggg      2760
agagaaggaa ctagcagaga aggaagaatg gaagaagagg gatggggaag agcaggagca      2820
aaaggagagg gagcagggcc atcagaagga agaaaccaa gagatggagg agggagggga      2880
ggaggagcat ggagaaggag aagaagagga gggagacaga gaagaggaag aagaaggga      2940 gggagaaggg aaagaggaag gagaagggga agaagtggag ggagaacgtg aaaaggagga      3000
aggagagagg aaaaggaggg aaagagcggg gaaggaggag aaggagaggg aagaaggaga      3060
ccaaggagag ggggaagagg aggaaacaga ggggagagga gaggaaaaag aggagggagg      3120
ggaagtagag ggagggggaag tagaggaggg gaaaggagag agggaagagg aagaggagga      3180
gggtgagggg gaagaggagg aaggggaggg ggaagagggag gaagggagg gggaagagga      3240 ggaaggagaa gggaaggggg aggaagaagg ggaagaagga gaagggggagg aagaagggga      3300 ggaaggagaa ggggagggg aaggaggaggga aggagaaggg gagggagaag aggaaggaga      3360
agggagggga gaagaggagg aaggagaagg ggagggagaa gaggaagggg aagaggaggg      3420
agaagaggag gaaggagaag ggaaagggga ggaggaagga gaggaaggag aaggggaggg      3480
ggaagaggag gaaggagaag gggaagggga ggatggagaa ggggagggg aagaggagga      3540 aggagaatgg gaggggaag aggaggaagg agaaggggag gggggaagagg aaggagaaga      3600 ggaagggag gaaggagaag gggagggga agaggaggaa ggagaagggg aggggggaga      3660
ggaggaaggg gaagaagaag gggaggaaga agagggagag gaggaagaag gggaggagga      3720
aggggaggaa gaagaggaag gggaagtgga aggggaggtg aaggggaggg aaggagaggg      3780
ggaaggagag gaagaggaag gagaggagga aggaagaagaa agggaaaagg aggggggaagg      3840 agaagaaaac aggaggaaca gagaagagga ggaggaagaa gagggaagt atcaggagac      3900 aggcgaagaa gagaatgaaa ggcaggatgg agaggagtac aaaaaagtga gcaaataaa      3960 aggatctgtg aaatatggca aacataaaac atatcaaaaa aagtcagtta ctaacacaca      4020
gggaaatggg aaagagcaga ggtccaaaat gccagtccag tcaaaacgac ttttaaaaaa      4080
cgggccatca ggttccaaaa agttctggaa taatgtatta ccacattact tggaattgaa      4140
gtaacaaacc ttaaatgtga cccgattatg gccagtcact cgagagatct aatctcgctt      4200
tcttgctgtc caatttctat taaaggttcc tttgttccct aagtccaact actaaactgg      4260
gggatattat gaagggcctt gagcatctgg attctgccta ataaaaaaca tttattttca      4320
ttgcaatgat gtatttaaat tatttctgaa tattttacta aaaagggaat gtgggaggtc      4380
agtgcattta aaacataaag aaagtagggg cgcgccagga accctagtg atggagttgg      4440 ccactccctc tctgcgcgct cgctcgctca ctgaggccgc ccgggcaaag cccgggcgtc      4500
gggcgacctt tggtcgcccg gcctcagtga gcgagcgagc gcgcagagag ggagtggcca      4560
a                                                                    4561
```

<210> SEQ ID NO 16
<211> LENGTH: 24

```
<212> TYPE: DNA
<213> ORGANISM: Artificial Sequence
<220> FEATURE:
<223> OTHER INFORMATION: Synthetic

<400> SEQUENCE: 16
ggacggatct gagggtgacg ggga                                              24

<210> SEQ ID NO 17
<211> LENGTH: 40
<212> TYPE: DNA
<213> ORGANISM: Artificial Sequence
<220> FEATURE:
<223> OTHER INFORMATION: Synthetic

<400> SEQUENCE: 17 gttttctcg agacgcatca ggcatggaga tgacttccct                              40

<210> SEQ ID NO 18
<211> LENGTH: 26
<212> TYPE: DNA
<213> ORGANISM: Artificial Sequence
<220> FEATURE:
<223> OTHER INFORMATION: Synthetic

<400> SEQUENCE: 18
agtgggagaa gcagaggatg ggcctg                                            26

<210> SEQ ID NO 19
<211> LENGTH: 46
<212> TYPE: DNA
<213> ORGANISM: Artificial Sequence
<220> FEATURE:
<223> OTHER INFORMATION: Synthetic

<400> SEQUENCE: 19
gttttctcga tggactggcc ataatcgggt cacatttaag gtttgt                      46

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
gcaccttctt gccactccta                                                   20

<210> SEQ ID NO 21
<211> LENGTH: 22
<212> TYPE: DNA
<213> ORGANISM: Artificial Sequence
<220> FEATURE:
<223> OTHER INFORMATION: Synthetic

<400> SEQUENCE: 21
gacacagcac caggctaaat cc                                                22

<210> SEQ ID NO 22
<211> LENGTH: 19
<212> TYPE: DNA
<213> ORGANISM: Artificial Sequence
<220> FEATURE:
<223> OTHER INFORMATION: Synthetic

<400> SEQUENCE: 22
```
cgtcctccgt gaccccggc                                                    19

<210> SEQ ID NO 23
<211> LENGTH: 1303
<212> TYPE: PRT
<213> ORGANISM: Mus musculus

<400> SEQUENCE: 23

Met Pro Arg Gly Ser Arg Trp Gly Ser Gln Gly Val Gly Gln His Leu
1               5                   10                  15

Arg Leu Asn Arg Val Ala Pro Ala Ile Phe Pro Lys Gln Ala Gln Ile
            20                  25                  30

Pro Phe Ala Gly Phe Gly Met Ala Glu Ser Glu Ser Leu Val Pro Asp
        35                  40                  45

Thr Gly Ala Val Phe Thr Phe Gly Lys Thr Lys Phe Ala Glu Asn Ile
    50                  55                  60

Pro Ser Lys Phe Trp Phe Lys Asn Asp Ile Pro Ile Cys Leu Ser Cys
65                  70                  75                  80

Gly Asp Glu His Thr Ala Ile Val Thr Gly Asn Asn Lys Leu Tyr Met
                85                  90                  95

Phe Gly Ser Asn Asn Trp Gly Gln Leu Gly Leu Gly Ser Lys Ala Ala
            100                 105                 110

Ile Ile Lys Pro Thr Cys Ile Lys Ala Leu Lys Pro Glu Lys Val Lys
        115                 120                 125

Leu Ala Ala Cys Gly Arg Asn His Thr Leu Val Ser Thr Asp Thr Gly
    130                 135                 140

Gly Val Tyr Ala Ala Gly Asn Asn Glu Gly Gln Leu Gly Leu Gly
145                 150                 155                 160

Asp Thr Asp Asp Arg Asp Thr Phe His Gln Ile Val Phe Phe Thr Pro
                165                 170                 175

Ala Asp Thr Ile Lys Gln Leu Ser Ala Gly Ala Asn Thr Ser Ala Ala
            180                 185                 190

Leu Thr Glu Asp Gly Lys Leu Phe Met Trp Gly Asp Asn Ser Glu Gly
        195                 200                 205

Gln Ile Gly Leu Glu Asp Lys Ser Asn Val Cys Ile Pro His Glu Val
    210                 215                 220

Thr Val Gly Lys Pro Ile Ser Trp Ile Ser Cys Gly Tyr Tyr His Ser
225                 230                 235                 240

Ala Phe Val Thr Met Asp Gly Glu Leu Tyr Thr Phe Gly Glu Pro Glu
                245                 250                 255

Asn Gly Lys Leu Gly Leu Pro Asn Glu Leu Leu Met Asn His Arg Ser
            260                 265                 270

Pro Gln Arg Val Leu Gly Ile Pro Glu Arg Val Ile Gln Val Ala Cys
        275                 280                 285

Gly Gly Gly His Thr Val Val Leu Thr Glu Lys Val Val Tyr Ala Phe
    290                 295                 300

Gly Leu Gly Gln Phe Gly Gln Leu Gly Leu Gly Thr Phe Leu Phe Glu
305                 310                 315                 320

Thr Ser Glu Pro Lys Ile Ile Glu Arg Ile Lys Asp Gln Lys Ile Cys
                325                 330                 335

His Ile Ser Cys Gly Glu Asn His Thr Ala Leu Met Thr Glu Leu Gly
            340                 345                 350

Leu Leu Tyr Thr Phe Gly Asp Gly Arg His Gly Lys Leu Gly Leu Gly
        355                 360                 365

```
Met Glu Asn Phe Thr Asn Gln Phe Phe Pro Thr Leu Cys Ser Asn Phe
    370                 375                 380

Leu Arg Phe Ala Val Gln Leu Ile Ala Cys Gly Gly Cys His Met Leu
385                 390                 395                 400

Val Phe Ala Thr Pro Arg Leu Gly Thr Ile Asp Glu Pro Lys Phe Glu
                405                 410                 415

Asp Val Tyr Glu Pro Tyr Ile Ser Thr Gly Ser Phe Ser Ile Asn Asp
            420                 425                 430

Leu Ser Pro Arg Ser Ser Leu Asn Arg Ser Leu Ser Ala Arg Leu Arg
        435                 440                 445

Arg Arg Glu Arg Glu Arg Pro Pro Cys Ser Ala Ser Met Val Gly Thr
450                 455                 460

Leu Pro Pro Leu Glu Gly Thr Ser Ala Ser Thr Ser Ala Tyr Phe Tyr
465                 470                 475                 480

Pro Ser Ser Pro Pro Phe His Leu Ser Val Asn Asn Tyr Pro Glu Lys
                485                 490                 495

Ser Pro Ser Glu Ser Met Glu Pro Leu Asp Ser Asp Tyr Phe Glu Asp
            500                 505                 510

Lys Met Asn Lys Asp Thr Glu Thr Glu Asn Ser Ser Ala Val Asp Ser
        515                 520                 525

Glu Asn Phe Gly Glu Thr Asn Asp Ile Leu Asn Met Thr His Met Met
    530                 535                 540

Thr Thr Ser Ser Asn Glu Lys Leu Leu Asp Phe Ser Pro Ile Gln Lys
545                 550                 555                 560

Gln Gln Asn Gln Asp Thr Phe Glu Lys Val Met Glu Ser Thr Pro Cys
                565                 570                 575

Thr Glu Asn Glu Asp Ser Tyr Glu Tyr Glu Glu Met Ser Lys Ile Lys
            580                 585                 590

Glu Val Thr Val Tyr Lys Gln Tyr Leu Ala Lys Gly Ile Tyr Met Ile
        595                 600                 605

Arg Pro Ala Glu Ile Leu Glu Ala Phe Ser Asp Glu Val Gly Asn
    610                 615                 620

Gly Leu Asp Gln Val Glu Glu Pro Arg Val Phe Thr Asp Gly Lys Gly
625                 630                 635                 640

Leu Gln Ser Lys Gln Val Gly Lys Glu Ser Asp Glu Ile Val Ser
                645                 650                 655

Glu Lys Lys Thr Glu Val Met Glu Val Ala Asp Val Lys Lys Ile Arg
            660                 665                 670

Glu Ser Glu Glu Asn Ser Lys Ser Asp Ser Leu Phe Asp Asp Leu Pro
        675                 680                 685

Asp Lys Thr Met Asn Ser Glu Ser Glu Asp Asn Lys Asp Ile Ala Glu
    690                 695                 700

Glu Arg Arg Ser Ser Glu Gln Asn Met Thr Phe Asp Ser Glu Thr Glu
705                 710                 715                 720

Leu Val Glu Glu Pro Asp Ser Tyr Met Glu Cys Glu Arg His Ser Glu
                725                 730                 735

Gln Asp Ser Ala Glu Glu Leu Glu Gln Pro Lys Leu Val Glu Tyr Ser
            740                 745                 750

Ser Glu Glu Lys Asp Glu Lys Asp Glu Lys Asp Asp Asp Glu Val Glu
        755                 760                 765

Thr Glu Asn Leu Trp Tyr Asp Arg Asn Cys Thr Glu Gln Glu Thr Glu
    770                 775                 780

Asn Val Phe Arg Ala Thr Arg Phe Phe Pro Lys Phe Asp Leu Lys His
```

```
                785                 790                 795                 800
Asp His Leu Ser Gly Ile Pro Glu Glu Gln Glu Gly Pro Asp Ser
                    805                 810                 815
Glu Gly Asn Val Val Glu Val Val Gln Ala Gln Lys Glu Asn
                820                 825                 830
Leu Glu Phe Glu Gly Asp Arg Lys Glu Ala Lys Ala Glu Ala Pro Ser
                    835                 840                 845
Asp Val Ile Thr Glu Lys Glu Val Ser Glu Ser Glu Arg Glu Ser Gly
            850                 855                 860
Gly Glu Arg Glu Asp Gly Ser Glu Gly Asp Gly Asp Gln Ile Cys Glu
865                 870                 875                 880
Lys Val Ser Leu Glu Thr Glu His Leu Gln Arg Ala Gln Lys Gln
                    885                 890                 895
Glu Arg Lys Lys Gly Lys Asp Lys Arg Ala Arg Cys Ile Leu Asp Met
                900                 905                 910
Lys Glu Arg Glu Glu Asp Lys Gly Trp Glu Lys Gly Ser Glu Gly Gly
                915                 920                 925
Asp Lys Met Lys Arg Asp Glu Gly Asn Gln Glu Lys Arg Lys Lys Glu
    930                 935                 940
Met Glu Glu Arg Asp Ala Gly Asp Glu Arg Ser Glu Glu Glu Glu Gly
945                 950                 955                 960
Glu Glu Glu Glu Pro Glu Glu Gly Glu Lys Glu Gly Gly Glu Glu
                    965                 970                 975
Glu Glu Gly Thr Ser Glu Asp Gln Ser Arg Glu Asp Glu Gly Asp Arg
            980                 985                 990
Gln Glu Lys Glu Gly Arg Arg Glu  Gly Lys Gly Arg Gln  Glu Asp Gly
            995                 1000                1005
Arg Glu  Gly Trp Lys Glu Gly  Glu Glu Gln Glu Gln  Glu Glu Glu
    1010                1015                1020
Ile Glu  Glu Gly Glu Glu Glu  Glu Arg Glu Gly Glu  Glu Glu Gly
    1025                1030                1035
Gly Glu  Glu Glu Gly Glu Gly  Glu Gly Glu Arg Glu  Glu Glu Gly
    1040                1045                1050
Glu Gly  Glu Glu Glu Gly Glu  Gly Glu Glu Glu Gly  Glu Gly Glu
    1055                1060                1065
Glu Glu  Gly Glu Gly Glu Glu  Gly Glu Gly Glu Glu  Glu Glu Gly
    1070                1075                1080
Glu Gly  Glu Glu Glu Gly Glu  Gly Glu Glu Glu Gly  Glu Gly Glu
    1085                1090                1095
Glu Asp  Gly Glu Gly Glu Glu  Asp Gly Glu Gly Glu  Glu Glu Gly
    1100                1105                1110
Glu Gly  Glu Glu Glu Gly Glu  Gly Glu Glu Glu Gly  Glu Gly Glu
    1115                1120                1125
Glu Glu  Gly Glu Gly Glu Gly  Glu Glu Glu Gly Glu  Gly Glu Glu
    1130                1135                1140
Glu Gly  Glu Gly Glu Glu Glu  Gly Glu Gly Glu Glu  Glu Gly Glu
    1145                1150                1155
Gly Glu  Glu Glu Gly Gly Glu  Asp Asp Glu Gly Glu  Glu Leu Glu
    1160                1165                1170
Lys Lys  Lys Gly Asp Ile Thr  Glu Glu Glu Glu Glu  Glu Glu Glu
    1175                1180                1185
Gly Gln  Glu Gly Asp Glu Arg  Glu Arg Glu Glu His  Gly Ser Cys
    1190                1195                1200
```

```
Glu Asp Asp Val Glu Glu Asp Lys Thr Tyr Asp Arg Glu Glu Gly
1205                1210                1215

Glu Tyr Lys Lys Ala Ile Gly Lys Val Ala Asp Asn Glu Ser Gln
1220                1225                1230

Glu Asp Arg Lys Gln Ser Pro Lys Val Ser Lys Ile Asn Gly Ser
1235                1240                1245

Met Lys Tyr Gly Arg His Gly Thr Tyr Ser Glu Lys Pro Ile Thr
1250                1255                1260

Asn Leu Gly Lys Thr Gln Pro Ser Lys Met Pro Met Glu Ser Arg
1265                1270                1275

Gln Leu Val Glu Asn Gly Leu Leu Gly Ser Glu Arg Phe Trp Ser
1280                1285                1290

Asp Val Leu Pro Leu Tyr Leu Glu Leu Lys
1295                1300

<210> SEQ ID NO 24
<211> LENGTH: 4932
<212> TYPE: DNA
<213> ORGANISM: Artificial Sequence
<220> FEATURE:
<223> OTHER INFORMATION: Synthetic

<400> SEQUENCE: 24
ctgcgcgctc gctcgctcac tgaggccgcc cgggcaaagc ccgggcgtcg ggcgaccttt       60
ggtcgcccgg cctcagtgag cgagcgagcg cgcagagagg gagtggccaa ctccatcact      120
aggggttcct gcgccgcctg ggccccagaa gcctggtggt tgtttgtcct tctcagggga      180
aaagtgaggc ggccccttgg aggaaggggc cgggcagaat gatctaatcg gattccaagc      240
agctcagggg attgtctttt tctagcacct tcttgccact cctaagcgtc ctccgtgacc      300
ccggctggga tttagcctgg tgctgtgtca gccccgggct cccaggggct tcccagtggt      360
ccccaggaac cctcgacagg gccagggcgt ctctctcgtc cagcaagggc agggacgggc      420
cacaggccaa gggccgcggc cgggaacggt gcattggaac gcggattccc cgtgccaaga      480
gtgacgtaag taccgcctat agagtctata ggcccacccc cttgctttta tttttttggtt     540 gggataaggc tggattattc tgagtccaag ctaggccctt ttgctaatca tcttcatacc      600
tcttatcttc ctcccacagc tcctgggcaa cgtgctggtc tgtgtgctgg cccatcactt      660
tggcaaagaa ttatcgatag ccaccatgcc aagagggtcg cgatgggggt cccaggggggt     720 agggcagcac cttaggctca atcgagtcgc ccctgctatc tttccgaagc aggcacagat      780
tccgttcgca ggcttcggca tggcggaatc tgagtcactg gtgcccgata caggtgctgt      840
gtttacgttt ggaaaaacta aatttgccga aaatattcct agcaaattct ggtttaaaaa      900
tgacataccc atatgtcttt catgtggaga tgaacatact gctattgtta caggaaataa      960
taaattgtac atgttcggca gtaacaactg gggtcagtta ggattaggat caaaagctgc     1020
tatcatcaag ccaacatgta tcaaagctct taagcctgag aaggtgaaac ttgctgcctg     1080
tggaaggaac cacaccttag tttcaacaga tactggtggc gtatatgcag ctggtggaaa     1140
taatgaaggt caactggggc ttggtgacac tgacgataga gacaccttc atcaaattgt      1200 cttcttttaca cctgctgata ccattaaaca gctctctgct ggcgccaata catccgctgc     1260
tcttactgag gatggaaaac ttttttatgtg gggtgacaat tctgaagggc agattggtct     1320
agaagataaa agtaatgtat gtatccctca tgaagtgact gttggaaagc caatttcctg     1380
gatctcttgt ggatattacc attcagcttt tgtaacaatg gatggagc tctacacatt       1440
```

```
tggagaaccc gagaatggga agttgggcct tcccaatgag ctgctgatga atcacagatc   1500 acccccagcgt gtgctgggca ttcctgagag ggtcattcaa gtggcctgtg gtggagggca   1560
cactgtggtt ctcacagaga aagttgtgta tgcctttggg ctggggcagt ttggacaact   1620
gggccttggc acttttctct ttgaaacatc agaacccaaa attattgagc gtattaagga   1680
tcagaaaata tgtcatattt cctgtggaga aaaccataca gctttgatga cagaactagg   1740
cctcctgtat acttttggag acggccgaca tggaaagtta ggacttggga tggagaattt   1800
caccaatcag ttctttccta ccttgtgctc taacttttg agatttgcag ttcaattgat   1860
tgcctgtggt ggatgtcata tgctagtttt tgccactcca cgacttggta caatagatga   1920
acctaaattt gaagacgtat atgagcctta taagtaca ggttcttttt ccatcaatga   1980
cctctcccca agaagttcac tgaatagatc tttatcagca cgtctgcggc gaagagagcg   2040
ggagagaccc ccatgctcag cttcaatggt gggaacactg cctccattag aggggacttc   2100
tgcctccact tcagcttatt tttaccccag ttcacccccc ttccatttgt ctgtgaataa   2160
ctacccagag aaaagcccct ctgaatcaat ggagccactg gactcagatt attttgaaga   2220
taaaatgaac aaagacacag agacagaaaa ttcttcagca gtggattcag aaaactttgg   2280
tgaaactaat gatatcttaa atatgacaca tatgatgact acgagttcca atgagaagtt   2340 attagattt tcaccaattc aaaaacaaca gaatcaagac acatttgaga aagtgatgga   2400
aagtacaccg tgcactgaaa atgaggatag ttatgaatat gaagaaatgt caaaaataaa   2460
agaagtgaca gtgtacaaac aatatttagc aaaagggatc tacatgatac gaccagccga   2520
gattctggaa gcattttcag atgaggaagt gggtaatggc ctagaccagg tggaggagcc   2580
gcgggtcttc actgatggaa agggcttaca aagcaagcaa gtaggaaagg aaagtgatga   2640
agaaatagtc tctgagaaga aaactgaggt gatggaagtg gcagatgtga aaaagattag   2700
agaaagtgaa gagaactcaa aatcagattc acttttttgat gacttaccag ataaaaccat   2760
gaattctgag agtgaagaca taaagatat tgctgaggaa aggagaagca gtgagcagaa   2820
tatgaccttt gacagtgaaa cagaattggt agaagaacca gacagttaca tggaatgtga   2880
gaggcacagt gagcaagaca gtgctgagga gttggagcag cccaagctag tagaaatatag   2940 tagcgaagag aaagatgaga aagatgagaa agatgacgat gaagtggaga ctgagaacttt   3000 atggtacgac aggaactgta ctgagcaaga aactgagaat gtattcagag caaccagatt   3060
tttcccaaag ttcgatctta agcatgatca tttgtcaggg ataccagagg agcaggaagg   3120
accagaggat tcagaaggaa atgtagtagt ggagcaagta gtacaggcac aaaaggaaaa   3180
tttggaattt gaaggagaca gaaaggaggc aaaagcagaa gccccatcag atgtcattac   3240
agaaaaagag gtgagtgaaa gtgagagaga gtcaggggggg gagagagagg acggatctga   3300
gggtgacggg gatcaaatct gtgagaaggt gagtttagaa acagagcatt tacaaagggc   3360
acagggaaaa caagagagga agaaaggtaa ggataaaaga gcaaggtgca tcctggatat   3420
gaaagagaga gaagaggata aaggatggga gaaagggagt gaaggaggag acaaaatgaa   3480
gagggatgaa ggaaaccaag agaaaaggaa gaaagagatg gaagaaagag atgcaggaga   3540
tgaaagaagt gaagaagagg aaggggagga agaagagcca agagagggg aaaagagga   3600 aggaggagag gaagaagaag gcacatcaga ggatcaaagt agggaggatg aaggagatag   3660
gcaagagaaa gaagggagaa gggaggggaa gggaaggcaa gaagatggga gagaagggtg   3720
gaaggaagga gaggagcaag aacaggagga ggaaatagag gaaggtgaag aggaagagag   3780
```

-continued

```
ggaaggagag gaagaagggg gagaggaaga gggggaaggc gaggggggaga gagaggaaga      3840 aggggaggga gaggaagagg gggagggaga ggaagaaggg gagggagagg aagagggga        3900 gggagaggaa gaagggagg gagaggaaga ggggaggggg gaggaagaag gggagggaga        3960
ggaagaaggg gagggagagg aagatgggga gggagaggaa gatgggagg gagaggaaga        4020 aggggaggga gaggaagaaa gggagggaga ggaagaaggg gaaggagagg aagaagggga      4080 ggggaggga gaagagagg gggagggaga atgggaggga gaggaagaag gggagggaga        4140
ggaagaaggg gagggagagg aagaagggga gggagaggaa gaagggagg gagaggaaga       4200 aggtggggaa gatgatgaag gagaggagct agaaaagaag aaaggagata ttacagagga     4260
agaagaggag gaggaagagg gacaagaagg ggatgaaaga gaagggaag aacacggaag       4320 ttgtgaggat gatgtggagg aagataaaac atatgacagg gaagaagggg aatacaagaa     4380
ggcaattgga aaagttgctg ataatgaaag tcaggaagac agaaaacaat ccccaaaagt     4440
aagtaaaata aatgggtcta tgaaatatgg cagacatggc acatactcag aaaagcccat     4500
tactaaccta gggaaaacac agccgtctaa aatgccaatg gagtccagac aacttgtaga    4560
gaatggcctc ctaggctccg aacgattctg gagtgatgtt ttaccactt atctggaatt      4620 gaagtaacag ggagtcatc tccatgcctg atgcgtctcg agattctgcc taataaaaaa      4680
catttatttt cattgcaatg atgtatttaa attatttctg aatatttac taaaaaggga     4740 atgtgggagg tcagtgcatt taaaacataa agaaagtagg gcgcgccagg aacccctagt    4800
gatggagttg gccactccct ctctgcgcgc tcgctcgctc actgaggccg cccgggcaaa     4860
gcccgggcgt cgggcgacct ttggtcgccc ggcctcagtg agcgagcgag cgcgcagaga    4920
gggagtggcc aa                                                          4932
```

<210> SEQ ID NO 25
<211> LENGTH: 1152
<212> TYPE: PRT
<213> ORGANISM: Artificial Sequence
<220> FEATURE:
<223> OTHER INFORMATION: Synthetic

<400> SEQUENCE: 25

```
Met Arg Glu Pro Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
            20                  25                  30

Lys Asn Asp Val Pro Val His Leu Ser Cys Gly Asp Glu His Ser Ala
        35                  40                  45

Val Val Thr Gly Asn Asn Lys Leu Tyr Met Phe Gly Ser Asn Asn Trp
    50                  55                  60

Gly Gln Leu Gly Leu Gly Ser Lys Ser Ala Ile Ser Lys Pro Thr Cys
65                  70                  75                  80

Val Lys Ala Leu Lys Pro Glu Lys Val Lys Leu Ala Ala Cys Gly Arg
                85                  90                  95

Asn His Thr Leu Val Ser Thr Glu Gly Gly Asn Val Tyr Ala Thr Gly
            100                 105                 110

Gly Asn Asn Glu Gly Gln Leu Gly Leu Gly Asp Thr Glu Glu Arg Asn
        115                 120                 125

Thr Phe His Val Ile Ser Phe Phe Thr Ser Glu His Lys Ile Lys Gln
    130                 135                 140

Leu Ser Ala Gly Ser Asn Thr Ser Ala Ala Leu Thr Glu Asp Gly Arg
145                 150                 155                 160
```

```
Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
            180                 185                 190

Ser Trp Ile Ser Cys Gly Tyr Tyr His Ser Ala Phe Val Thr Thr Asp
        195                 200                 205

Gly Glu Leu Tyr Val Phe Gly Glu Pro Glu Asn Gly Lys Leu Gly Leu
    210                 215                 220

Pro Asn Gln Leu Leu Gly Asn His Arg Thr Pro Gln Leu Val Ser Glu
225                 230                 235                 240

Ile Pro Glu Lys Val Ile Gln Val Ala Cys Gly Gly Glu His Thr Val
                245                 250                 255

Val Leu Thr Glu Asn Ala Val Tyr Thr Phe Gly Leu Gly Gln Phe Gly
            260                 265                 270

Gln Leu Gly Leu Gly Thr Phe Leu Phe Glu Thr Ser Glu Pro Lys Val
        275                 280                 285

Ile Glu Asn Ile Arg Asp Gln Thr Ile Ser Tyr Ile Ser Cys Gly Glu
    290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335

His Phe Ile Pro Thr Leu Cys Ser Asn Phe Leu Arg Phe Ile Val Lys
            340                 345                 350

Leu Val Ala Cys Gly Gly Cys His Met Val Val Phe Ala Ala Pro His
        355                 360                 365

Arg Gly Val Ala Lys Glu Ile Glu Phe Asp Glu Ile Asn Asp Thr Cys
    370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Arg Glu Arg Glu
                405                 410                 415

Arg Ser Pro Asp Ser Phe Ser Met Arg Arg Thr Leu Pro Pro Ile Glu
            420                 425                 430

Gly Thr Leu Gly Leu Ser Ala Cys Phe Leu Pro Asn Ser Val Phe Pro
        435                 440                 445

Arg Cys Ser Glu Arg Asn Leu Gln Glu Ser Val Leu Ser Glu Gln Asp
    450                 455                 460

Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
                485                 490                 495

Thr Asp Ile Leu Asn Met Thr His Ile Met Ser Leu Asn Ser Asn Glu
            500                 505                 510

Lys Ser Leu Lys Leu Ser Pro Val Gln Lys Gln Lys Gln Gln Thr
        515                 520                 525

Ile Gly Glu Leu Thr Gln Asp Thr Ala Leu Thr Glu Asn Asp Asp Ser
    530                 535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
                565                 570                 575
```

```
Glu Ala Phe Ser Asp Glu Val Glu Ile Pro Glu Lys Glu Gly
            580                 585                 590
Ala Glu Asp Ser Lys Gly Asn Gly Ile Glu Gln Glu Val Glu Ala
            595                 600                 605
Asn Glu Glu Asn Val Lys Val His Gly Gly Arg Lys Glu Lys Thr Glu
610                 615                 620
Ile Leu Ser Asp Asp Leu Thr Asp Lys Ala Glu Val Ser Glu Gly Lys
625                 630                 635                 640
Ala Lys Ser Val Gly Glu Ala Glu Asp Gly Pro Glu Gly Arg Gly Asp
                645                 650                 655
Gly Thr Cys Glu Glu Gly Ser Ser Gly Ala Glu His Trp Gln Asp Glu
            660                 665                 670
Glu Arg Glu Lys Gly Glu Lys Asp Lys Gly Arg Gly Glu Met Glu Arg
            675                 680                 685
Pro Gly Glu Gly Glu Lys Glu Leu Ala Glu Lys Glu Glu Trp Lys Lys
            690                 695                 700
Arg Asp Gly Glu Glu Gln Glu Gln Lys Glu Arg Glu Gln Gly His Gln
705                 710                 715                 720
Lys Glu Arg Asn Gln Glu Met Glu Glu Gly Glu Glu His Gly
            725                 730                 735
Glu Gly Glu Glu Glu Glu Gly Asp Arg Glu Glu Glu Glu Lys Glu
            740                 745                 750
Gly Glu Gly Lys Glu Glu Gly Glu Glu Val Glu Gly Glu Arg
            755                 760                 765
Glu Lys Glu Glu Gly Glu Arg Lys Lys Glu Glu Arg Ala Gly Lys Glu
            770                 775                 780
Glu Lys Gly Glu Glu Gly Asp Gln Gly Glu Gly Glu Glu Glu
785                 790                 795                 800
Thr Glu Gly Arg Gly Glu Lys Glu Glu Gly Glu Val Glu Gly
            805                 810                 815
Gly Glu Val Glu Glu Gly Lys Gly Glu Arg Glu Glu Glu Glu Glu
            820                 825                 830
Gly Glu Gly Glu Glu Gly Glu Gly Gly Glu Glu Glu Gly Glu
            835                 840                 845
Gly Glu Glu Glu Gly Glu Gly Lys Gly Glu Glu Glu Gly Glu Glu
850                 855                 860
Gly Glu Gly Glu Glu Glu Gly Glu Glu Glu Glu Glu Gly Glu Glu
865                 870                 875                 880
Glu Glu Gly Glu Gly Glu Gly Glu Glu Gly Glu Gly Glu Gly Glu
                885                 890                 895
Glu Glu Glu Gly Glu Gly Glu Gly Glu Glu Gly Glu Glu Glu Gly
                900                 905                 910
Glu Glu Glu Glu Gly Glu Gly Lys Gly Glu Glu Glu Gly Glu Glu Gly
            915                 920                 925
Glu Gly Glu Gly Glu Glu Glu Gly Glu Gly Glu Gly Glu Asp Gly
            930                 935                 940
Glu Gly Glu Gly Glu Glu Glu Gly Glu Trp Gly Glu Glu
945                 950                 955                 960
Glu Gly Glu Gly Glu Gly Glu Glu Glu Glu Gly Glu Glu
                965                 970                 975
Gly Glu Gly Glu Gly Glu Glu Glu Gly Glu Gly Glu Glu
            980                 985                 990
Glu Glu Gly Glu Glu Glu Gly Glu  Glu Glu Gly Glu Gly  Glu Glu Glu
```

| | | | | | | | | | | | |
|---|---|---|---|---|---|---|---|---|---|---|---|
| | | 995 | | | | 1000 | | | | 1005 | |
| Gly | Glu | Gly | Glu | Gly | Glu | Glu | Glu | Glu | Gly | Glu | Val Glu Gly |
| | | 1010 | | | | 1015 | | | | 1020 | |
| Glu | Val | Glu | Gly | Glu | Gly | Glu | Gly | Glu | Gly | Glu | Glu Glu Glu |
| | | 1025 | | | | 1030 | | | | 1035 | |
| Gly | Glu | Glu | Glu | Gly | Glu | Glu | Arg | Glu | Lys | Glu | Gly Gly Glu |
| | | 1040 | | | | 1045 | | | | 1050 | |
| Glu | Asn | Arg | Arg | Asn | Arg | Glu | Glu | Glu | Glu | Glu | Glu Gly Lys |
| | | 1055 | | | | 1060 | | | | 1065 | |
| Tyr | Gln | Glu | Thr | Gly | Glu | Glu | Asn | Glu | Arg | Gln | Asp Gly Glu |
| | | 1070 | | | | 1075 | | | | 1080 | |
| Glu | Tyr | Lys | Lys | Val | Ser | Lys | Ile | Lys | Gly | Ser | Val Lys Tyr Gly |
| | | 1085 | | | | 1090 | | | | 1095 | |
| Lys | His | Lys | Thr | Tyr | Gln | Lys | Lys | Ser | Val | Thr | Asn Thr Gln Gly |
| | | 1100 | | | | 1105 | | | | 1110 | |
| Asn | Gly | Lys | Glu | Gln | Arg | Ser | Lys | Met | Pro | Val | Gln Ser Lys Arg |
| | | 1115 | | | | 1120 | | | | 1125 | |
| Leu | Leu | Lys | Asn | Gly | Pro | Ser | Gly | Ser | Lys | Lys | Phe Trp Asn Asn |
| | | 1130 | | | | 1135 | | | | 1140 | |
| Val | Leu | Pro | His | Tyr | Leu | Glu | Leu | Lys | | | |
| | | 1145 | | | | 1150 | | | | | |

<210> SEQ ID NO 26
<211> LENGTH: 4561
<212> TYPE: DNA
<213> ORGANISM: Artificial Sequence
<220> FEATURE:
<223> OTHER INFORMATION: Synthetic

<400> SEQUENCE: 26

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct gcggccgctg ggccccagaa gcctggtggt tgtttgtcct tctcagggga     180
aaagtgaggc ggccccttgg aggaaggggc cgggcagaat gatctaatcg gattccaagc     240
agctcagggg attgtctttt tctagcacct tcttgccact cctaagcgtc ctccgtgacc     300
ccggctggga tttagcctgg tgctgtgtca gccccgggct cccaggggct cccagtggt      360
ccccaggaac cctcgacagg gccagggcgt ctctctcgtc cagcaagggc agggacgggc     420
cacaggccaa gggccgcggc cgggaacggt gcattggaac gcggattccc cgtgccaaga     480
gtgacgtaag taccgcctat agagtctata ggcccacccc cttgctttta ttttttggtt     540
gggataaggc tggattattc tgagtccaag ctaggccctt ttgctaatca tcttcatacc     600
tcttatcttc ctcccacagc tcctgggcaa cgtgctggtc tgtgtgctgg cccatcactt     660
tggcaaagaa ttatcgatag ccaccatgag ggagccggaa gagctgatgc ccgattcggg     720
tgctgtgttt acatttggga aaagtaaatt tgctgaaaat aatcccggta aattctggtt     780
taaaaatgat gtccctgtac atctttcatg tggagatgaa cattctgctg ttgttaccgg     840
aaataataaa ctttacatgt ttggcagtaa caactgggt cagttaggat taggatcaaa     900
gtcagccatc agcaagccaa catgtgtcaa agctctaaaa cctgaaaaag tgaaattagc     960
tgcctgtgga aggaaccaca ccctggtgtc aacagaagga ggcaatgtat atgcaactgg    1020
tggaaataat gaaggacagt tggggcttgg tgacaccgaa gaaagaaaca cttttcatgt    1080
aattagcttt tttacatccg agcataagat taagcagctg tctgctggat ctaatacttc    1140
```

```
agctgcccta actgaggatg gaagactttt tatgtggggt gacaattccg aagggcaaat    1200
tggtttaaaa aatgtaagta atgtctgtgt ccctcagcaa gtgaccattg ggaaacctgt    1260
ctcctggatc tcttgtggat attaccattc agcttttgta acaacagatg gtgagctata    1320
tgtgttgga gaacctgaga atgggaagtt aggtcttccc aatcagctcc tgggcaatca    1380
cagaacaccc cagctggtgt ctgaaattcc ggagaaggtg atccaagtag cctgtggtgg    1440
agagcatact gtggttctca cggagaatgc tgtgtatacc tttgggctgg acaatttgg    1500
tcagctgggt cttggcactt ttcttttga aacttcagaa cccaaagtca ttgagaatat    1560
tagggatcaa acaataagtt atatttcttg tggagaaaat cacacagctt tgataacaga    1620
tatcggcctt atgtatactt ttggagatgg tcgccacgga aaattaggac ttggactgga    1680
gaattttacc aatcacttca ttcctacttt gtgctctaat tttttgaggt ttatagttaa    1740
attggttgct tgtggtggat gtcacatggt agttttgct gctcctcatc gtggtgtggc    1800
aaaagaaatt gaattcgatg aaataaatga tacttgctta tctgtggcga cttttctgcc    1860
gtatagcagt ttaacctcag gaaatgtact gcagaggact ctatcagcac gtatgcggcg    1920
aagagagagg gagaggtctc cagattcttt ttcaatgagg agaacactac ctccaataga    1980
agggactctt ggccttttctg cttgttttct ccccaattca gtcttttccac gatgttctga    2040
gagaaacctc caagagagtg tcttatctga acaggacctc atgcagccag aggaaccaga    2100
ttatttgcta gatgaaatga ccaaagaagc agagatagat aattcttcaa ctgtagaaag    2160
ccttggagaa actactgata tcttaaacat gacacacatc atgagcctga attccaatga    2220
aaagtcatta aaattatcac cagttcagaa acaaagaaa caacaaacaa ttggggaact    2280
gacgcaggat acagctctta ctgaaaacga tgatagtgat gaatatgaag aaatgtcaga    2340
aatgaaagaa gggaaagcat gtaaacaaca tgtgtcacaa gggattttca tgacgcagcc    2400
agctacgact atcgaagcat tttcagatga ggaagtagag atcccagagg agaaggaagg    2460
agcagaggat tcaaaaggaa atggaataga ggagcaagag gtagaagcaa atgaggaaaa    2520
tgtgaaggtg catggaggaa gaaggagaa aacagagatc ctatcagatg accttacaga    2580
caaagcagag gtgagtgaag gcaaggcaaa atcagtggga gaagcagagg atgggcctga    2640
aggtagaggg gatggaacct gtgaggaagg tagttcagga gcagaacact ggcaagatga    2700
ggagagggag aagggggaga aagacaaggg tagaggagaa atggagaggc aggagagggg    2760
agagaaggaa ctagcagaga aggaagaatg gaagaagagg gatggggaag agcaggagca    2820
aaaggagagg gagcagggcc atcagaagga aagaaaccaa gagatggagg agggagggga    2880
ggaggagcat ggagaaggag aagaagagga gggagacaga gaagaggaag aagagaagga    2940
gggagaaggg aaagaggaag gagaagggga agaagtggag ggagaacgtg aaaaggagga    3000
aggagagagg aaaaggagg aaagagcggg gaaggaggag aaaggagagg aagaaggaga    3060
ccaaggagag gggaagagg aggaaacaga ggggagagga gaggaaaaag aggagggagg    3120
ggaagtagag ggagggaaag tagaggaggg gaaaggagag agggaagagg aagaggagga    3180
gggtgagggg gaagaggagg aaggggaggg ggaagaggag gaagggaggg ggaagaggaa    3240
ggaaggagaa gggaaggggg aggagaaagg ggaagaagga gaagggaggg aagaagggga    3300
ggaaggagaa gggaggggg aagaggagga aggagaaggg gagggagaag aggaaggaga    3360
aggggaggga gaagagaggg aaggagaagg ggagggagaa gaggaaggag aaggggaggg    3420
agaagaggag gaaggagaag gggaaagggga ggaggaagga gaggaaggag aaggggaggg    3480
```

```
ggaagaggag gaaggagaag gggaaggggga ggatggagaa ggggaggggg aagaggagga      3540
aggagaatgg gaggggggaag aggaggaagg agaaggggag ggggaagagg aaggagaagg     3600
ggaaggggag gaaggagaag gggagggggga agaggaggaa ggagaagggg aggggggaaga    3660
ggaggaaggg gaagaagaag gggaggaaga aggagagggga gaggaagaag gggaggggaga    3720
aggggaggaa gaagaggaag gggaagtggaa aggggaggtg gaagggggagg aaggagaggg    3780
ggaaggagag gaagaggaag gagggaggga aggagaagaa agggaaaagg aggggggaagg     3840
agaagaaaac aggaggaaca gagaagagga ggaggaagaa gaggggaagt atcaggagac      3900
aggcgaagaa gagaatgaaa ggcaggatgg agaggagtac aaaaaagtga gcaaaataaa      3960
aggatctgtg aaatatggca aacataaaac atatcaaaaa aagtcagtta ctaacacaca      4020
gggaaatggg aaagagcaga ggtccaaaat gccagtccag tcaaaacgac ttttaaaaaa      4080
cgggccatca ggttccaaaa agttctggaa taatgtatta ccacattact tggaattgaa      4140
gtaacaaacc ttaaatgtga cccgattatg gccagtcact cgagagatct aatctcgctt      4200
tcttgctgtc caatttctat taaaggttcc tttgttccct aagtccaact actaaactgg      4260
gggatattat gaagggcctt gagcatctgg attctgccta ataaaaaaca tttattttca      4320
ttgcaatgat gtatttaaat tatttctgaa tattttacta aaaagggaat gtgggaggtc      4380
agtgcattta aaacataaag aaagtagggg cgcgccagga acccctagtg atggagttgg      4440
ccactccctc tctgcgcgct cgctcgctca ctgaggccgc ccgggcaaag cccgggcgtc      4500
gggcgacctt tggtcgcccg gcctcagtga gcgagcgagc gcgcagagag ggagtggcca     4560
a                                                                       4561

<210> SEQ ID NO 27
<211> LENGTH: 3459
<212> TYPE: DNA
<213> ORGANISM: Artificial Sequence
<220> FEATURE:
<223> OTHER INFORMATION: Synthetic

<400> SEQUENCE: 27
atgagggagc cggaagagct gatgcccgat tcgggtgctg tgtttacatt tgggaaaagt        60
aaatttgctg aaaataatcc cggtaaattc tggtttaaaa atgatgtccc tgtacatctt       120
tcatgtggag atgaacattc tgctgttgtt accggaaata taaactttta catgtttggc       180
agtaacaact ggggtcagtt aggattagga tcaaagtcag ccatcagcaa gccaacatgt       240
gtcaaagctc taaacctga aaaagtgaaa ttagctgcct gtggaaggaa ccacaccctg        300
gtgtcaacag aaggaggcaa tgtatatgca actggtggaa ataatgaagg acagttgggg       360
cttggtgaca ccgaagaaag aaacactttt catgtaatta gcttttttac atccgagcat       420
aagattaagc agctgtctgc tggatctaat acttcagctg ccctaactga ggatggaaga       480
ctttttatgt ggggtgacaa ttccgaaggg caaattggtt taaaaaatgt aagtaatgtc       540
tgtgtccctc agcaagtgac cattgggaaa cctgtctcct ggatctcttg tggatattac       600
cattcagctt ttgtaacaac agatggtgag ctatatgtgt ttggagaacc tgagaatggg       660
aagttaggtc ttcccaatca gctcctgggc aatcacagaa cacccagct ggtgtctgaa        720
attccggaga aggtgatcca agtagcctgt ggtggagagc atactgtggt tctcacggag       780
aatgctgtgt atacctttgg gctgggacaa tttggtcagc tgggtcttgg cactttttctt     840
tttgaaactt cagaacccaa agtcattgag aatattaggg atcaaacaat aagttatatt      900
tcttgtggag aaaatcacac agctttgata acagatatcg gccttatgta ctactttgga     960
```

-continued

```
gatggtcgcc acggaaaatt aggacttgga ctggagaatt ttaccaatca cttcattcct    1020
actttgtgct ctaattttt gaggtttata gttaaattgg ttgcttgtgg tggatgtcac    1080
atggtagttt ttgctgctcc tcatcgtggt gtggcaaaag aaattgaatt cgatgaaata    1140
aatgatactt gctatctgt ggcgactttt ctgccgtata gcagtttaac ctcaggaaat    1200
gtactgcaga ggactctatc agcacgtatg cggcgaagag agagggagag gtctccagat    1260 tcttttcaa tgaggagaac actacctcca atagaaggga ctcttggcct ttctgcttgt    1320
tttctcccca attcagtctt tccacgatgt tctgagagaa acctccaaga gagtgtctta    1380
tctgaacagg acctcatgca gccagaggaa ccagattatt tgctagatga aatgaccaaa    1440
gaagcagaga tagataattc ttcaactgta gaaagccttg agaaactac tgatatctta    1500 aacatgacac acatcatgag cctgaattcc aatgaaaagt cattaaaatt atcaccagtt    1560
cagaaacaaa agaaacaaca acaattggg gaactgacgc aggatacagc tcttactgaa    1620
aacgatgata gtgatgaata tgaagaaatg tcagaaatga agaagggaa agcatgtaaa    1680 caacatgtgt cacaagggat tttcatgacg cagccagcta cgactatcga agcattttca    1740
gatgaggaag tagagatccc agaggagaag gaaggagcag aggattcaaa ggaaatgga    1800 atagaggagc aagaggtaga agcaaatgag gaaaatgtga aggtgcatgg aggaagaaag    1860
gagaaaacag agatcctatc agatgaccttacagacaaag cagaggtgag tgaaggcaag    1920
gcaaaatcag tgggagaagc agaggatggg cctgaaggta gaggggatgg aacctgtgag    1980
gaaggtagtt caggagcaga acactggcaa gatgaggaga gggagaaggg ggagaaagac    2040
aagggtagag gagaaatgga gaggccagga gagggagaga aggaactagc agagaaggaa    2100
gaatggaaga gagggatgg ggaagagcag gagcaaaagg agagggagca gggccatcag    2160
aaggaaagaa accaagagat ggaggaggga ggggaggagg agcatggaga aggagaagaa    2220
gaggagggag acagagaaga ggaagaagag aaggagggag aagggaaaga ggaaggagaa    2280
ggggaagaag tggagggaga acgtgaaaag gaggaaggag agaggaaaaa ggaggaaaga    2340
gcggggaagg aggagaaagg agaggaagaa ggagaccaag gagagggga agaggaggaa    2400 acagagggga gaggagagga aaaagaggag ggaggggaag tagagggagg ggaagtagag    2460
gaggggaaag gagagaggga agaggaagag gaggagggtg aggggaaga ggaggaaggg    2520 gaggggaag aggaggaagg ggaggggaa gaggaggaag gagaagggaa aggggaggaa    2580
gaaggggaag aaggagaagg ggaggaagaa ggggaggaag gagaaggga ggggaagag    2640 gaggaaggag aaggggaggg agaagaggaa ggagaagggg agggagaaga ggaggaagga    2700 gaagggagg gagaagagga aggagaaggg gagggagaag aggaggaagg agaagggaaa    2760
ggggaggagg aaggagagga aggagaaggg gagggggaag aggaggaagg agaagggaa    2820 ggggaggatg gagaagggga ggggaagag gaggaaggag aatgggaggg ggaagaggag    2880
gaaggagaag ggagggga agaggaagga gaagggga gggaggaagg agaagggag    2940 ggggaagagg aggaaggaga aggggagggg gaagaggagg aaggggaaga gaaggggag    3000 gaagaaggag agggagagga agaagggag ggagaagggg aggaagaaga ggaagggga    3060 gtggaagggg aggtggaagg ggaggaagga gaggggaag gagaggaaga ggaaggagag    3120
gaggaaggag aagaaaggga aaaggagggg gaaggagaag aaaacaggag gaacagagaa    3180
gaggaggagg aagaagaggg gaagtatcag gagacaggcg aagaagagaa tgaaaggcag    3240
gatggagagg agtacaaaaa agtgagcaaa ataaaaggat ctgtgaaata tggcaaacat    3300
```

| | | | | |
|---|---|---|---|---|
| aaaacatatc | aaaaaaagtc | agttactaac | acacagggaa | atgggaaaga gcagaggtcc | 3360 |
| aaaatgccag | tccagtcaaa | acgactttta | aaaaacgggc | catcaggttc caaaaagttc | 3420 |
| tggaataatg | tattaccaca | ttacttggaa | ttgaagtaa | | 3459 |

RP2 AND RPGR VECTORS FOR TREATING X-LINKED RETINITIS PIGMENTOSA

CROSS-REFERENCE TO RELATED APPLICATIONS

This patent application is a U.S. National Stage of PCT/US2016/022072, filed Mar. 11, 2016, which claims the benefit of U.S. Provisional Patent Application No. 62/131,661, filed Mar. 11, 2015, each of which is incorporated by reference in its entirety herein.

STATEMENT REGARDING FEDERALLY SPONSERED RESEARCH AND DEVELOPMENT

This invention was made with Government support under project number 1ZIAEY000443 by the National Institutes of Health, National Eye Institue. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 77,678 Byte ASCII (Text) file named 73045_ST25.txt dated Sep. 7, 2017.

BACKGROUND OF THE INVENTION

X-linked retinitis pigmentosa (XLRP) is an X-linked, hereditary retinal dystrophy characterized by a progressive loss of photoreceptor cells, leading to vision impairment or blindness. XLRP may involve rod photoreceptor death, followed by cone cell death. As a result, an XLRP patient usually experiences an early onset of night-blindness, followed by a gradual but progressive loss of peripheral vision, and an eventual loss of central vision. There is currently no treatment for XLRP. Accordingly, there exists a need for compositions and methods for treating XLRP.

BRIEF SUMMARY OF THE INVENTION

An embodiment of the invention provides an adeno-associated virus (AAV) vector comprising (a) a nucleotide sequence encoding RP2 or a functional fragment thereof and (b) an AAV2 Inverted Terminal Repeat (ITR) or a functional fragment thereof.

Another embodiment of the invention provides an AAV vector comprising a nucleotide sequence encoding RPGR-ORF15 or a functional fragment or functional variant thereof, wherein (i) the vector further comprises a CMV/human β-globin intron and/or a human β-globin polyadenylation signal; and (ii) the nucleotide sequence encoding RPGR-ORF15 or a functional fragment or a functional variant thereof is optionally under the transcriptional control of a rhodopsin kinase promoter.

Additional embodiments of the invention provide related pharmaceutical compositions and methods of making the AAV vector comprising a nucleotide sequence encoding RPGR-ORF15 or a functional fragment or functional variant thereof.

Another embodiment of the invention provides a method of treating or preventing X-linked retinitis pigmentosa (XLRP) in a mammal in need thereof, the method comprising administering to the mammal the inventive vector or pharmaceutical composition in an amount effective to treat or prevent XLRP in the mammal.

Still another embodiment of the invention provides a method of increasing photoreceptor number in a retina of a mammal, the method comprising administering to the mammal the inventive vector or pharmaceutical composition in an amount effective to increase photoreceptor number in the retina of the mammal.

DETAILED DESCRIPTION OF THE INVENTION

In accordance with an embodiment of the invention, it has been discovered that an AAV vector comprising a nucleotide sequence encoding RP2 or RPGR-ORF15 effectively preserved the function and viability of photoreceptors in mouse models of XLRP.

Approximately 15% of XLRP patients have a mutation in the Retinitis Pigmentosa 2 (RP2) gene. The human RP2 gene has five exons and encodes a protein of 350 amino acid residues. RP2 protein is a GTPase activating protein (GAP) for arginine adenosine-5'-diphosphoribosylation (ADP-ribosylation) factor-like 3 (ARL3), a microtubule-associated small GTPase that localizes to the connecting cilium of photoreceptors. An example of a complementary DNA (cDNA) sequence encoding the human RP2 protein is the nucleotide sequence of SEQ ID NO: 1. An example of a protein sequence encoding the human RP2 protein is the amino acid sequence of SEQ ID NO: 2.

An embodiment of the invention provides an AAV vector comprising a nucleic acid comprising (a) a nucleotide sequence encoding RP2 or a functional fragment thereof and (b) an AAV2 ITR or a functional fragment thereof. The nucleotide sequence encoding RP2 may be any suitable nucleotide sequence that encodes RP2 from any species. In a preferred embodiment, the RP2 is human RP2. In an embodiment of the invention, the nucleotide sequence encoding human RP2 comprises a nucleotide sequence that encodes a human RP2 protein comprising the amino acid sequence of SEQ ID NO: 2. In an embodiment of the invention, the nucleotide sequence encoding human RP2 comprises the nucleotide sequence of SEQ ID NO: 1.

Approximately 75% of XLRP patients have a mutation in the Retinitis Pigmentosa GTPase Regulator (RPGR) gene. Multiple RPGR transcripts have been detected in the retina. A majority of the disease-causing mutations have been detected in a variant isoform RPGR-ORF15, which is expressed in the retina. RPGR-ORF15 protein interacts with centrosome-cilia proteins and localizes to the connecting cilia in both rod and cone photoreceptors. An example of a cDNA sequence encoding the wild-type human RPGR-ORF15 protein is die nucleotide sequence of SEQ ID NO: 27. An example of a protein sequence encoding the wild-type human RPGR-ORF15 protein is the amino acid sequence of SEQ ID NO: 4. An example of a cDNA sequence encoding a functional variant of the wild-type human RPGR-ORF15 protein is the nucleotide sequence of SEQ ID NO: 3. An example of a protein sequence encoding a functional variant of the wild-type human RPGR-ORF15 protein is the amino acid sequence of SEQ ID NO: 25.

Another embodiment of the invention provides an AAV vector comprising a nucleic acid comprising a nucleotide sequence encoding RPGR-ORF15 or a functional fragment or functional variant thereof, wherein (i) the vector further comprises a CMV/human β-globin intron and/or a human β-globin polyadenylation signal; and (ii) the nucleotide sequence encoding RPGR-ORF15 or a functional fragment or a functional variant thereof is optionally under the transcriptional control of a rhodopsin kinase promoter. In an embodiment of the invention, the AAV vector comprising a nucleic acid comprising a nucleotide sequence encoding RPGR-ORF15 or a functional fragment or functional variant thereof, wherein (i) the nucleotide sequence encoding human RPGR-ORF15 or a functional fragment or functional variant thereof is under the transcriptional control of a rhodopsin kinase promoter, and/or (ii) the vector further comprises a CMV/human β-globin intron and/or a human β-globin polyadenylation signal. The nucleotide sequence encoding wild-type RPGR-ORF15 may be any suitable nucleotide sequence that encodes wild-type RPGR-ORF15 from any species. In a preferred embodiment, the RPGR-ORF15 is human RPGR-ORF15. In an embodiment of the invention, the nucleotide sequence encoding wild-type human RPGR-ORF15 comprises a nucleotide sequence that encodes a wild-type human RPGR-ORF15 protein comprising the amino acid sequence of SEQ ID NO: 4. In an embodiment of the invention, the nucleotide sequence encoding wild-type human RPGR-ORF15 protein comprises the nucleotide sequence of SEQ ID NO: 27. The nucleotide sequence encoding a functional variant of a wild-type RPGR-ORF15 may be any suitable nucleotide sequence that encodes a functional variant of the wild-type RPGR-ORF15. In a preferred embodiment, the functional variant of the RPGR-ORF15 is a functional variant of human RPGR-ORF15. In an embodiment of the invention, the nucleotide sequence encoding a functional variant of the wild-type human RPGR-ORF15 comprises a nucleotide sequence that encodes a functional variant of the wild-type human RPGR-ORF15 protein comprising the amino acid sequence of SEQ ID NO: 25. In an embodiment of the invention, the nucleotide sequence encoding a functional variant of the wild-type human RPGR-ORF15 protein comprises the nucleotide sequence of SEQ ID NO: 3. Hereinafter, wild-type RPGR-ORF15 and functional variants of wild-type RPGR-ORF15 will be collectively referred to as "RPGR-ORF15," unless specified otherwise.

The AAV vector may be suitable for packaging into any AAV serotype or variant thereof that is suitable for administration to ocular cells. Examples of suitable AAV serotypes may include, but are not limited to, AAV1, AAV2, AAV3, AAV4, AAV5, AAV6, AAV7, AAV8, AAV9, and any variant thereof. Preferably, the AAV vector is packaged into serotype AAV8 or AAV9.

The AAV vector may be packaged in a capsid protein, or fragment thereof, of any of the AAV serotypes described herein. Preferably, the vector is packaged in an AAV8 capsid. In an embodiment of the invention, the AAV8 capsid comprises the amino acid sequence of SEQ ID NO: 5.

A suitable recombinant AAV may be generated by culturing a packaging cell which contains a nucleic acid sequence encoding an AAV serotype capsid protein, or fragment thereof, as defined herein; a functional rep gene; any of the inventive vectors described herein; and sufficient helper functions to permit packaging of the inventive vector into the AAV capsid protein. The components required by the packaging cell to package the inventive AAV vector in an AAV capsid may be provided to the host cell in trans. Alternatively, any one or more of the required components (e.g., inventive vector, rep sequences, capsid sequences, and/or helper functions) may be provided by a stable packaging cell which has been engineered to contain one or more of the required components using methods known to those of skill in the art.

In an embodiment of the invention, the AAV vector is self-complementary. Self-complementary vectors may, advantageously, overcome the rate-limiting step of second-strand DNA synthesis and confer earlier onset and stronger gene expression. Preferably, the AAV vector comprising a nucleotide sequence encoding RP2 is self-complementary. In an embodiment, the vector comprises single-stranded DNA.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In an embodiment, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green et al. (eds.), *Molecular Cloning, A Laboratory Manual*, $4^{th}$ Edition, Cold Spring Harbor Laboratory Press, New York (2012). For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxynethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

In an embodiment of the invention, the vector is a recombinant expression vector. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vectors of the invention can be prepared using standard recombinant DNA techniques described in, for example, Green et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The vector may further comprise regulatory sequences which are operably linked to the nucleotide sequence encoding RP2 or RPGR-ORF15 in a manner which permits one or more of the transcription, translation, and expression of RP2 or RPGR-ORF15 in a cell transfected with the vector or infected with a virus that comprises the vector. As used herein, "operably linked" sequences include both regulatory sequences that are contiguous with the nucleotide sequence encoding RP2 or RPGR-ORF15 and regulatory sequences that act in trans or at a distance to control the nucleotide sequence encoding RP2 or RPGR-ORF15.

The regulatory sequences may include appropriate transcription initiation, termination, promoter and enhancer sequences; RNA processing signals such as splicing and polyadenylation (polyA) signal sequences; sequences that stabilize cytoplasmic mRNA; sequences that enhance translation efficiency (i.e., Kozak consensus sequence); sequences that enhance protein stability; and when desired, sequences that enhance secretion of the encoded product. PolyA signal sequences may be synthetic or may be derived from many suitable species, including, for example, SV-40, human and bovine. Preferably, the vector comprises a full-length or truncated human beta (β)-globin polyA signal sequence. In an embodiment of the invention, the human β-globin polyA signal sequence comprises the nucleotide sequence of SEQ ID NO: 6 (full-length) or SEQ ID NO: 7 (truncated).

The regulatory sequences may also include an intron. Preferably, the intron is positioned between the promoter sequence and the nucleotide sequence encoding RP2 or RPGR-ORF15. Examples of suitable intron sequences include a cytomegalovirus (CMV)/human β-globin intron and an intron derived from SV-40 (referred to as SD-SA). Preferably, the intron is a CMV/human β-globin intron. In an embodiment of the invention, the CMV/human β-globin intron comprises the nucleotide sequence of SEQ ID NO: 8 or 9.

The regulatory sequences may also include a promoter. The promoter may be any promoter suitable for expressing RP2 or RPGR-ORF15 in a target cell, e.g., an ocular cell. The promoter may be inducible or constitutive. In an embodiment of the invention, the promoter is suitable for expressing RP2 or RPGR-ORF15 in a particular ocular cell type. In this regard, the promoter may be cell-specific. For example, the promoter may be specific for expression in any one or more of ocular cells, retinal pigment epithelium (RPE) cells, photoreceptor cells, in rods, or in cones. Examples of suitable promoters include, but are not limited to, the human G-protein-coupled receptor protein kinase 1 (GRK1) promoter (also referred to as the human rhodopsin kinase promoter), the human interphotoreceptor retinoid-binding protein proximal (IRBP) promoter, the native promoter for RP2 or RPGR-ORF15, the RPGR proximal promoter, the rod opsin promoter, the red-green opsin promoter, the blue opsin promoter, the cGMP-β-phosphodiesterase promoter, the mouse opsin promoter, the rhodopsin promoter, the alpha-subunit of cone transducin, beta phosphodiesterase (PDE) promoter, the retinitis pigmentosa (RP1) promoter, the NXNL2/NXNL1 promoter, the RPE65 promoter, the retinal degeneration slow/peripherin 2 (Rds/perphZ) promoter, the VMD2 promoter, and functional fragments of any of the foregoing. Preferably, the nucleotide sequence encoding RP2 or RPGR-ORF15 is under the transcriptional control of the GRK1 promoter (also referred to as human rhodopsin kinase promoter). In an embodiment of the invention, the human rhodopsin kinase promoter comprises the nucleotide sequence of SEQ ID NO: 10.

In an embodiment of the invention, the vector comprises an ITR or a functional fragment thereof. Preferably, the vector comprises a 5' and a 3' AAV ITR. The ITRs may be of any suitable AAV serotype, including any of the AAV serotypes described herein. The ITRs may be readily isolated using techniques known in the art and may be isolated or obtained from public or commercial sources (e.g., the American Type Culture Collection, Manassas, Va.). Alternatively, the ITR sequences may be obtained through synthetic or other suitable means by reference to published sequences. Preferably, the vector comprises a 5' and a 3' AAV2 ITR. In an embodiment of the invention, the vector comprises a truncated 5' AAV2 ITR. In an embodiment of the invention, the vector comprises a 5' AAV2 ITR comprising the nucleotide sequence of SEQ ID NO: 11 and a 3' AAV2 ITR comprising the nucleotide sequence of SEQ ID NO: 12. In another embodiment of the invention, the vector comprises a truncated 5' AAV2 ITR comprising the nucleotide sequence of SEQ ID NO: 13 and a 3' AAV2 ITR comprising the nucleotide sequence of SEQ ID NO: 12.

Included in the scope of the invention are vectors comprising functional fragments of any of the nucleotide sequences described herein that encode functional fragments of the proteins described herein. The term "functional fragment," when used in reference to a RP2 or RPGR-ORF15 protein, refers to any part or portion of the protein, which part or portion retains the biological activity of the protein of which it is a part (the parent protein). Functional protein fragments encompass, for example, those parts of a protein that retain the ability to recognize treat or prevent XLRP, increase photoreceptor number, decrease retinal detachment in a mammal, increase the electrical response of a photoreceptor in a mammal, increase protein expression in a retina of a mammal, localize protein to rod outer segments in a retina of a mammal, or increase visual acuity in a mammal, to a similar extent, the same extent, or to a higher extent, as the parent protein. For example, a functional fragment of a nucleotide sequence encoding RPGR-ORF15 may be a cDNA encoding RPGR-ORF15 but shortened by 654 base pairs (bp) in the repetitive region, which has been shown to reconstitute RPGR function in mice (Hong et al., *Invest. Ophthalmol. Vis. Sci.*, 46(2): 435-441 (2005)).

The term "functional fragment" when used in reference to a polyA signal sequence or an ITR, refers to any part or portion of the nucleotide sequence, which part or portion retains the biological activity of the nucleotide sequence of which it is a part (the parent nucleotide sequence). Functional protein fragments encompass, for example, those parts of a polyA signal sequence that retain the ability to be recognized by a RNA cleavage complex or those parts of an ITR that retain the ability to allow for replication to a similar extent, the same extent, or to a higher extent, as the parent nucleotide sequence. In reference to the parent nucleotide sequence or protein, the functional fragment can comprise, for instance, about 10%, 25%, 30%, 50%, 68%, 80%, 90%, 95%, or more, of the parent nucleotide sequence or protein.

Included in the scope of the invention are vectors encoding functional variants of the RP2 and RPGR-ORF15 proteins described herein. The term "functional variant," as used herein, refers to a protein having substantial or significant sequence identity or similarity to a parent protein, which functional variant retains the biological activity of the protein of which it is a variant. Functional variants encompass, for example, those variants of the RP2 or RPGR-ORF15 proteins described herein (the parent protein) that retain the ability to treat or prevent XLRP, increase photoreceptor number, decrease retinal detachment in a mammal, increase the electrical response of a photoreceptor in a mammal, increase protein expression in a retina of a mammal, localize protein to rod outer segments in a retina of a mammal, and/or increase visual acuity in a mammal to a similar extent, the same extent, or to a higher extent, as the parent RP2 or RPGR-ORF15 protein. In reference to the parent RP2 or RPGR-ORF15 protein, the functional variant can, for instance, be at least about 30%, about 50%, about 75%, about 80%, about 85%, about 90%, about 91%, about 92%, about 93%, about 94%, about 95%, about 96%, about 97%, about 98%, about 99% or more identical in amino acid sequence to the parent RP2 or RPGR-ORF15 protein.

A functional variant can, for example, comprise the amino acid sequence of the parent RP2 or RPGR-ORF15 protein with at least one conservative amino acid substitution. Alternatively or additionally, the functional variants can comprise the amino acid sequence of the parent RP2 or RPGR-ORF15 protein with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent RP2 or RPGR-ORF15 protein.

Amino acid substitutions of the parent RP2 or RPGR-ORF15 protein are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The RP2 or RPGR-ORF15 protein or functional variant can consist essentially of the specified amino acid sequence or sequences described herein, such that other components, e.g., other amino acids, do not materially change the biological activity of the RP2 or RPGR-ORF15 protein or functional variant.

In an embodiment of the invention, the RP2 vector comprises a nucleotide sequence comprising the components set forth in Table 1. In this regard, the full-length RP2 vector may comprise the nucleotide sequence of SEQ ID NO: 14.

TABLE 1

| RP2 vector (SEQ ID NO: 14) | | |
|---|---|---|
| Nucleotide Position of SEQ ID NO: 14 | SEQ ID NO: | Component |
| 1-106 | 13 | 5' AA V2 ITR (truncated) |
| 137-432 | 10 | human rhodopsin kinase promoter |
| 446-730 | 9 | CMV/human β-globin intron |
| 759-1811 | 1 | human RP2 cDNA |
| 1817-1930 | 7 | human β-globin polyadenylation signal (truncated) |
| 1943-2087 | 12 | 3' AAV2 ITR |

In an embodiment of the invention, the vector encoding a functional variant of wild-type human RPGR-ORF15 comprises a nucleotide sequence comprising the components set forth in Table 2. In this regard, the full-length vector encoding a functional variant of wild-type human RPGR-ORF15 (SEQ ID NO: 25) may comprise the nucleotide sequence of SEQ ID NO: 15.

TABLE 2

| Functional Variant of Wild-Type Human RPGR-ORF15 vector (SEQ ID NO: 15) | | |
|---|---|---|
| Nucleotide Position of SEQ ID NO: 15 | SEQ ID NO: | Element |
| 1-130 | 11 | 5' AAV2 Inverted Terminal Repeat (ITR) |
| 140-434 | 10 | human rhodopsin kinase promoter |
| 449-668 | 8 | cytomegalovirus (CMV)/human β-globin intron |
| 686-4144 | 3 | functional variant of wild-type human RPGR-ORF15 cDNA |

TABLE 2-continued

Functional Variant of Wild-Type Human RPGR-ORF15 vector (SEQ ID NO: 15)

| Nucleotide Position of SEQ ID NO: 15 | SEQ ID NO: | Element |
|---|---|---|
| 4194-4403 | 6 | human β-globin polyadenylation signal |
| 4417-4561 | 12 | 3' AAV2 ITR |

In an embodiment of the invention, the vector encoding wild-type human RPGR-ORF15 comprises a nucleotide sequence comprising the components set forth in Table 3. In this regard, the full-length vector encoding wild-type human RPGR-ORF15 (SEQ ID NO: 4) may comprise the nucleotide sequence of SEQ ID NO: 26.

TABLE 3

Wild-Type Human RPGR-ORF15 vector (SEQ ID NO: 26)

| Nucleotide Position of SEQ ID NO: 26 | SEQ ID NO: | Element |
|---|---|---|
| 1-130 | 11 | 5' AAV2 Inverted Terminal Repeat (ITR) |
| 140-434 | 10 | human rhodopsin kinase promoter |
| 449-668 | 8 | cytomegalovirus (CMV)/human β-globin intron |
| 686-4144 | 27 | wild-type human RPGR-ORF15 cDNA |
| 4194-4403 | 6 | human β-globin polyadenylation signal |
| 4417-4561 | 12 | 3' AAV2 ITR |

An embodiment of the invention provides an AAV vector comprising a nucleic acid comprising a nucleotide sequence encoding mouse RPGR-ORF15 or a functional fragment thereof. The nucleotide sequence encoding mouse RPGR-ORF15 may comprise a nucleotide sequence encoding a mouse RPGR-ORF15 protein comprising the amino acid sequence of SEQ ID NO: 23. The vector may further comprise regulatory sequences which are operably linked to the nucleotide sequence encoding mouse RPGR-ORF15 as described herein with respect to other aspects of the invention. In an embodiment of the invention, the AAV vector comprising a nucleic acid comprising a nucleotide sequence encoding mouse RPGR-ORF15 comprises the nucleotide sequence of SEQ ID NO: 24.

In an embodiment of the invention, the vector may also comprise a nucleotide sequence that is about 70% or more, e.g., about 80% or more, about 90% or more, about 91% or more, about 92% or more, about 93% or more, about 94% or more, about 95% or more, about 96% or more, about 97% or more, about 98% or more, or about 99% or more identical to any of the nucleotide sequences described herein.

An embodiment of the invention provides a method of making any of the AAV vectors comprising a nucleotide sequence encoding RPGR-ORF15 or a functional fragment or functional variant thereof described herein. The method may comprise amplifying the purine-rich region of RPGR-ORF15 or a functional variant thereof using genomic DNA as a template. Amplifying may be carried out by any suitable method known in the art. For example, the amplifying may be carried out by PCR. The method may comprise ligating the purine-rich region to a nucleotide sequence encoding exons 1 to 14 of RPGR-ORF15 or a functional variant thereof. Ligating may be carried out by any suitable method known in the art (see, e.g., Greene supra). The method may further comprise propagating the vector in a XL10-gold bacterial strain.

The inventive vectors can be formulated into a composition, such as a pharmaceutical composition. In this regard, the invention provides a pharmaceutical composition comprising any of the vectors described herein, and a pharmaceutically acceptable carrier. Any suitable carrier can be used within the context of the invention, and such carriers are well known in the art. The choice of carrier will be determined, in part, by the particular site to which the composition is to be administered (e.g., ocular cells, RPE cells, photoreceptor cells, rods, and cones) and the particular method used to administer the composition. The pharmaceutical composition can optionally be sterile or sterile with the exception of the one or more adeno-associated viral vectors.

Suitable formulations for the pharmaceutical composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the pharmaceutical composition for use in the inventive method is formulated to protect the adeno-associated viral vectors from damage prior to administration. For example, the pharmaceutical composition can be formulated to reduce loss of the adeno-associated viral vectors on devices used to prepare, store, or administer the expression vector, such as glassware, syringes, or needles. The pharmaceutical composition can be formulated to decrease the light sensitivity and/or temperature sensitivity of the adeno-associated viral vectors. To this end, the pharmaceutical composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition may extend the shelf life of the vector, facilitate administration, and increase the efficiency of the inventive method. A pharmaceutical composition also can be formulated to enhance transduction efficiency of the adeno-associated viral vector. In addition, one of ordinary skill in the art will appreciate that the pharmaceutical composition can comprise other therapeutic or biologically-active agents. For example, factors that control inflammation, such as ibuprofen or steroids, can be part of the pharmaceutical composition to reduce swelling and inflammation associated with in vive administration of the adeno-associated viral vectors. Antibiotics, i.e., microbicides and fungicides, can be present to treat existing infection and/or reduce the risk of future infection, such as infection associated with gene transfer procedures.

It is contemplated that the inventive vectors and pharmaceutical compositions (hereinafter referred to collectively as "inventive AAV vector materials") can be used in methods of treating or preventing XLRP. In this regard, an embodiment of the invention provides a method of treating or preventing XLRP in a mammal comprising administering to the mammal any of the inventive AAV vector materials described herein, in an amount effective to treat or prevent the XLRP in the mammal.

The terms "treat" and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount or any level of treatment or prevention of XLRP in a mammal. Furthermore, the treatment or prevention provided by the inventive method can include treatment or prevention of one or more conditions, symptoms, or signs of XLRP. In some cases, the inventive methods may cure XLRP. Also, for purposes herein, "prevention" can encompass delaying the onset of XLRP, or a symptom, sign, or condition thereof.

For example, the inventive methods may ameliorate, correct or stop the progression of any one or more of a loss of photoreceptor structure and/or function; thinning or thickening of the outer nuclear layer (ONL); thinning or thickening of the outer plexiform layer (OPL); shortening of the rod and cone inner segments; retraction of bipolar cell dendrites; thinning or thickening of the inner retinal layers including inner nuclear layer, inner plexiform layer, ganglion cell layer and nerve fiber layer; opsin mislocalization; overexpression of neurofilaments; retinal detachment in a mammal, decrease in the electrical response of a photoreceptor in a mammal, loss of electroretinography (ERG) function; loss of visual acuity and contrast sensitivity; loss of visually guided behavior; decreased peripheral vision, decreased central vision, decreased night vision, loss of contrast sensitivity, and loss of color perception.

The inventive methods, vectors and pharmaceutical compositions may provide any one or more advantages. For example, the inventive methods, vectors and pharmaceutical compositions may improve the health or quality of the retina and may reduce or prevent vision impairment. Accordingly, the inventive methods, vectors and pharmaceutical compositions may, advantageously, improve a patient's ability to carry out vision-guided activities such as, for example, driving an automobile and living independently.

It is contemplated that the inventive vectors and pharmaceutical compositions can be used in methods of increasing photoreceptor number in a retina of a mammal. In this regard, an embodiment of the invention provides a method of increasing photoreceptor number in a retina of a mammal, the method comprising administering to the mammal any of the inventive AAV vector materials described herein, in an amount effective to increase photoreceptor number in the retina of the mammal.

The inventive vectors and pharmaceutical compositions may also be useful for increasing visual acuity in a mammal. In this regard, an embodiment of the invention provides a method of increasing visual acuity of a mammal, the method comprising administering to the mammal any of the inventive AAV vector materials described herein, in an amount effective to increase visual acuity in the mammal.

The inventive vectors and pharmaceutical compositions may also be useful for decreasing retinal detachments in a mammal. In this regard, an embodiment of the invention provides a method of decreasing retinal detachment in a mammal, the method comprising administering to the mammal any of the inventive AAV vector materials described herein, in an amount effective to decrease retinal detachment in the mammal.

The inventive vectors and pharmaceutical compositions may also be useful for increasing the electrical response of a photoreceptor in a mammal. In this regard, an embodiment of the invention provides a method of increasing the electrical response of a photoreceptor in a mammal, the method comprising administering to the mammal any of the inventive AAV vector materials described herein, in an amount effective to increase the electrical response of a photoreceptor in the mammal. The photoreceptor may include, for example, one or both of rods and cones. The electrical response of a photoreceptor may be measured by any suitable method known in the art such as, for example, electroretinography (ERG).

Another embodiment of the invention provides a method of increasing expression of a protein in a retina of a mammal. The method may comprise administering to the mammal any of the inventive AAV RP2 vectors described herein or a pharmaceutical composition comprising the vector in an amount effective to increase expression of the protein in the retina of the mammal. In an embodiment of the invention, the protein is RP2, cone opsin, or cone PDE6.

Another embodiment of the invention provides a method of increasing expression of a protein in a retina of a mammal, the method comprising administering to the mammal any of the inventive RPGR vectors described herein or a pharmaceutical composition comprising the vector in an amount effective to increase expression of a protein in the retina of the mammal. In an embodiment of the invention, the protein is RPGR.

Another embodiment of the invention provides a method of localizing a protein to the rod outer segments in the retina of a mammal. The method may comprise administering to the mammal any of the inventive RPGR vectors described herein or a pharmaceutical composition comprising the vector in an amount effective to localize the protein to the rod outer segments in the retina of the mammal. In an embodiment of the invention, the protein is rhodopsin or PDE6.

The inventive methods may comprise administering the AAV vector material to the eye of the mammal, for example, intraocularly, subretinally, or intravitreally. Preferably, the AAV vector material is administered subretinally.

For purposes of the invention, the amount or dose of the inventive AAV vector material administered should be sufficient to effect a desired response, e.g., a therapeutic or prophylactic response, in the mammal over a reasonable time frame. For example, the dose of the inventive AAV vector material should be sufficient to treat or prevent XLRP, increase photoreceptor number, and/or increase visual acuity, in a period of from about 2 hours or longer, e.g., 12 to 24 or more hours, from the time of administration. In certain embodiments, the time period could be even longer. The dose will be determined by the efficacy of the particular inventive AAV vector material and the condition of the mammal (e.g., human), as well as the body weight of the mammal (e.g., human) to be treated.

Many assays for determining an administered dose are known in the art. An administered dose may be determined in vitro (e.g., cell cultures) or in vivo (e.g., animal studies). For example, an administered dose may be determined by determining the $IC_{50}$ (the dose that achieves a half-maximal inhibition of signs of disease), $LD_{50}$ (the dose lethal to 50% of the population), the $ED_{50}$ (the dose therapeutically effective in 50%, of the population), and the therapeutic index in cell culture, animal studies, or combinations thereof. The therapeutic index is the ratio of $LD_{50}$ to $ED_{50}$ (i.e., $LD_{50}/ED_{50}$).

The dose of the inventive AAV vector material also may be determined by the existence, nature, and extent of any adverse side effects that might accompany the administration of a particular inventive AAV vector material. Typically, the attending physician will decide the dosage of the inventive AAV vector material with which to treat each individual patient, taking into consideration a variety of factors, such as age, body weight, general health, diet, sex, inventive AAV vector material to be administered, route of administration, and the severity of the condition being treated. By way of example and not intending to limit the invention, the dose of the inventive AAV vector material can be about $1 \times 10^8$ to about $2.5 \times 10^8$ vector genomes (vg) per eye, about $1 \times 10^8$ to about $1 \times 10^9$ vector genomes (vg) per eye, or about $1 \times 10^6$ to about $1 \times 10^{13}$ vg per eye. In an embodiment of the invention, the dose of the inventive RP2 vector is about $5 \times 10^6$ to about $5 \times 10^{12}$, about $5 \times 10^6$ to about $5 \times 10^{12}$, or about $5 \times 10^7$ to about $5 \times 10^8$ vector genomes (vg) per eye. In another embodiment of the invention, the dose of the inventive RPGR-ORF15 vector is about $5 \times 10^6$ to about $5 \times 10^{12}$, about $1 \times 10^8$ to about $5 \times 10^9$ vg per eye, preferably about $5 \times 10^8$ to about $2 \times 10^9$ vg per eye. A dose of the inventive RPGR-ORF15 vector of about $1 \times 10^9$ vg per eye is especially preferred. In another embodiment of the invention, the dose of the inventive mouse RPGR-ORF15 vector is about $1 \times 10^8$ to about $5 \times 10^8$ vg per eye, preferably about $3 \times 10^8$ vg per eye.

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

Examples 1-6

The following materials and methods were employed for Examples 1-6:

Mouse Line and Husbandry

Rpgr-knockout (KO) mice were maintained in National Institutes of Health (NIH) animal care facilities in controlled ambient illumination on a 12 hour (h) light/12 h dark cycle. Studies conform to Association for Research in Vision and Ophthalmology (ARVO) statement for the Use of Animals in Ophthalmic and Vision Research. Animal protocols were approved by National Eye Institute (NEI) Animal Care and Use Committee.

AAV Vector Construction and Production

The purine-rich region of the mouse or human RPGR-ORF15 exon was polymerase chain reaction (PCR)-amplified from the genomic DNA of a male C57 mouse or a healthy adult male donor, respectively. The 3' DNA of exon ORF15 including a Sap I restriction enzyme site and the adjacent purine-rich region was PCR amplified from genomic DNA of a healthy adult male donor. Sequences of the primers are as follows:

mRpgr forward (F): SEQ ID NO: 16;
mRpgr reverse (R): SEQ ID NO: 17;
hRPGR F: SEQ ID NO: 18; and
hRPGR R: SEQ ID NO: 19.

PCR was performed with PRIMESTAR HS DNA Polymerase (Clontech Laboratories, Inc., Mountain View, Calif.). The PCR conditions were 94° C. for 1 minute followed by 30 cycles at 98° C. for 10 seconds and 72° C. for 80 seconds; followed by 7 minutes of extension at 72° C. and hold at 4° C. The PCR products were verified by sequencing (Sequetech Inc., Redwood City, Calif.) and ligated to the synthetic upstream exons to generate a full length human or mouse RPGR-ORF15 cDNA. Exons 1 to 14 and 5' part of exon ORF15 with the Sap I site was synthesized. The PCR-amplified and the synthesized DNA fragments were digested with Sap I respectively, and then ligated to assemble the full-length human RPGR-ORF15 cDNA (SEQ ID NO: 3). Mouse full-length Rpgr-ORF15 cDNA was generated using the same strategy.

AAV type 2 inverted terminal repeats (ITRs) (SEQ ID NOs: 11 and 12) were used in the AAV vector construction. The RPGR-ORF15 expression cassettes included a human rhodopsin kinase promoter (SEQ ID NO: 10) (Khani et al., *Invest. Ophthalmol. Vis. Sci.,* 48: 3954-3961 (2007)), a chimeric CMV/human β-globin intron (SEQ ID NO: 8), the human (SEQ ID NO: 3) or mouse RPGR-ORF15 cDNA and a human β-globin polyadenylation site (SEQ ID NO: 6). The vector plasmids were propagated in a XL10-gold bacterial strain (Agilent Technologies, Inc., Santa Clara, Calif.).

AAV vectors were produced by triple-plasmid transfection to HEK293 cells, as described in (Grimm et al., *Blood,* 102: 2412-2419 (2003)). The human RPGR-ORF15 AAV construct was packaged into AAV8, while the mouse Rpgr-ORF15 construct was packaged into both AAV8 and AAV9. The vectors were purified by polyethylene glycol precipitation followed by cesium chloride density gradient fractionation, as described in Grimm, supra. Purified vectors were formulated in 10 mM Tris-HCl, 180 mM NaCl, pH 7.4, quantified by real-time PCR using linearized plasmid standards, and stored at −80° C. until use. Integrity of the vectors was examined each time after purification by amplifying the purine-rich region of the RPGR-ORF15 cDNA.

Subretinal Injections

AAV vectors were injected subretinally, as described in Sun et al., *Gene Ther.,* 17: 117-131 (2010) but with some modifications. Briefly, mice were anesthetized by intraperitoneal injection of ketamine (80 mg/kg) and xylazine (8 mg/kg). Pupils were dilated with topical atropine (1%) and tropicamide (0.5%). Surgery was performed under an ophthalmic surgical microscope. A small incision was made through the cornea adjacent to the limbus using 18-gauge needle. A 33-gauge blunt needle fitted to a Hamilton syringe was inserted through the incision while avoiding the lens and pushed through the retina. All injections were made subretinally in a location within the nasal quadrant of the retina. Each animal received 1 µl of AAV vector at the concentration of $1 \times 10^{11}$ to $1 \times 10^{13}$ vector genomes per ml. Treatment vectors were given in the right eye, and control vehicle was injected in the fellow eye. Visualization during injection was aided by addition of fluorescein (100 mg/ml AK-FLUOR, Alcon, Fort Worth, Tex.) to the vector suspensions at 0.1% by volume. The dose efficacy studies were carried out on more than 100 Rpgr-knockout (KO) mice.

Immunoblot Analysis

Mouse retinas were homogenized in radioimmunoprecipitation assay (RIPA) lysis buffer containing 1× proteinase inhibitor by brief sonication. The tissue debris was removed by a brief centrifugation. Retinal protein was separated on sodium dodecyl sulfate (SDS)-polyacrylamide gel by electrophoresis and transferred to nitrocellulose membranes. After pre-adsorption with 5% nonfat dry milk for 1 h at room temperature, the membrane blots were incubated overnight at 4° C. with the primary antibody. The blots were then washed with Tris buffered saline with the TWEEN 20 detergent (TBST: 137 mM Sodium Chloride, 20 mM Tris, 0.1% Tween-20, pH 7.6), incubated for 1 h at room temperature with the secondary antibody-horseradish peroxidase conjugated goat anti-rabbit or anti-mouse IgG (Jackson Immunoresearch, West Grove, Pa.), and developed by SUPERSIGNAL West Pico Chemiluminescent (Thermo Fisher Scientific Inc., Rockford, Ill.). The primary antibodies used in this study were: rabbit anti-mouse RPGR-ORF15 antibody C100 and rabbit anti-human RPGR antibody 643, which recognize the C-terminal of the mouse RPGR-ORF15 and a common region of human RPGR-ORF15 and RPGR$^{1-19}$ isoforms, respectively. Mouse monoclonal anti-β-actin antibody (Sigma) was used for loading controls.

Tissue Processing, Immunofluorescence and Morphometric Analysis

After euthanasia, mouse eyes were harvested. A blue dye was used to mark the orientation of the eye before enucleation to ensure that immunostaining was performed on equivalent areas on vector-treated and vehicle-treated eyes. For fixation, eyes were immediately placed in 4% paraformaldehyde for 1 h. The fixed tissues were soaked in 30% sucrose/PBS overnight, quickly frozen and sectioned at 10-μm thickness using cryostat. An alternative protocol was used to detect RPGR localization to the connecting cilia, as described in Hong et al., *Invest. Ophthalmol. Vis. Sci.*, 44: 2413-2421 (2003). Briefly, eyes were embedded in optimal cutting temperature compound (OCT) without fixation and quick-frozen in liquid nitrogen. Cryosections were cut at 10 μm and collected on pretreated glass slides (Superfrost Plus; Fisher Scientific, Pittsburgh, Pa.). Sections were stored at −80° C. and used within 2 to 3 days. Just before use, sections were fixed on slides for 2 min with 1% formaldehyde in phosphate-buffered saline (PBS) at pH 7.0. If sections were stored for longer than 1 week, an additional treatment was performed in 0.1% 2-mercaptomethanol (in PBS) for 5 minutes (min), followed by 1% formaldehyde fixation for 5 min. Sections were then washed once in PBS and carried through to immunofluorescence staining.

For immunofluorescence staining, the cryosections were pre-adsorbed in 5% goat serum in PBS containing 0.1% Triton X-100 (PBST) for 1 h, and then incubated overnight at 4° C. in primary antibody diluted in 5% goat serum, as described in Hong et al., *Invest. Ophthalmol. Vis. Sci.*, 44: 2413-2421 (2003). Sections were washed three times in PBST and incubated with fluorochrome-conjugated secondary antibodies and 0.2 μg/ml DAPI (4',6-diamidino-2-phenylindole) for 1 h. Sections were washed again and mounted in FLUOROMOUNT-G mounting medium (SouthernBiotech, Birmingham, Ala.). Images were captured using a fluorescence microscope AXIO IMAGER Z1 or a confocal scanning microscope LSM700 (Zeiss, Germany).

The primary antibodies included the poly-clonal rabbit anti-human RPGR-ORF15 antibody 636 and rabbit anti-mouse RPGR-ORF15 antibody S1 (Hong et al., *Invest. Ophthalmol. Vis. Sci.*, 43: 3373-3382 (2002)), which recognize the common region of RPGR-ORF15 and RPGR$^{1-19}$ isoforms in human and mouse, respectively. Other primary antibodies used in this study include monoclonal antibody for rhodopsin (1D4, Santa Cruz Biotechnology, Dallas, Tex.) and M-cone opsin (Millipore, Billerica, Mass.). Secondary antibodies included goat anti-rabbit and anti-mouse antibodies conjugated with ALEXA FLUOR 555 and 568 dyes (Life Technologies, Grand Island, N.Y.).

For morphometric analyses of outer nuclear layer (ONL) thickness, measurements were made along the vertical meridian at four locations to each side of the optic nerve head separated by 500 μm each. Measurements began at about 500 μm from the optic nerve head itself.

Electroretinogram (ERG)

Mice were dark-adapted overnight. Anesthesia and pupil dilation were conducted as described above. A computer-based system (ESPION E2 electroretinography system, Diagnosys LLC, Lowell, Mass.) was used for ERG recordings in response to flashes produced with light-emitting diode (LED) or Xenon bulbs. Corneal ERGs were recorded from both eyes using gold wire loop electrodes with a drop of 2.5% hypromellose ophthalmic demulcent solution. A gold wire loop placed in the mouth was used as reference, and a ground electrode was on the tail. The ERG protocol consisted of recording dark-adapted ERGs using brief flashes of −2 to +3 log sc cd·s·m$^{-2}$/flash. Responses were computer averaged and recorded at 3 to 60 second (s) intervals depending upon the stimulus intensity. Light-adapted ERGs were recorded after 2 min of adaptation to a white 32 cd·m$^{-2}$ rod-suppressing background. ERGs were recorded for stimulus intensities of −0.52 to +2 log sc cd·s·m$^{-2}$.

Optical Coherence Tobmography (OCT)

OCT volume scan images were acquired with a spectral domain (SD) OCT system (SPECTRALIS system, Heidelberg Engineering, Carlsbad, Calif.). Mice were anesthetized and pupils were dilated as described above. The optic nerve head was centered within ~1.0 mm diameter field of view. Retinal thickness maps were generated by Heidelberg Eye Explorer software.

Statistical Analysis

Two-tailed paired t-test was used to compare outcomes in vector-treated versus vehicle-treated eyes. GRAPHPAD Prism 6 software (GraphPad Software, La Jolla, Calif.) was used for statistical analysis.

Example 1

This example demonstrates the generation of mouse and human RPGR-ORF15 AAV vectors.

AAV vectors carrying either a mouse or a human RPGR-ORF15 expression cassette were constructed. Previous efforts to obtain a full-length RPGR-ORF15 cDNA using reverse transcription PCR had not been successful due to the purine-rich region of the terminal ORF15 exon. To overcome this problem, regular PCR was conducted using genomic DNA as a template to amplify the purine-rich region, and then the purine-rich region was ligated to a synthetic DNA fragment encoding the upstream exons. This strategy was adopted for obtaining both mouse and human RPGR-ORF15 cDNA. Sequencing of the complete cDNA was performed to validate the products. A human rhodopsin kinase (RK) promoter (SEQ ID NO: 10), which shows rod and cone cell specificity (Khani et al., *Invest. Ophthalmol. Vis. Sci.*, 48: 3954-3961 (2007)), was used to drive RPGR-ORF15 expression. These two vectors were packaged into AAV type 8 and are hereafter referred to as AAV8-mRpgr and AAV8-hRPGR, respectively. The mouse RPGR-ORF15 vector was also packaged into AAV type 9 (hereafter referred to AAV9-mRpgr), a serotype that transduces cones of non-human primate efficiently (Vandenberghe et al., *PLoS Pne*, 8: e53463 (2013)).

The vector plasmids containing the purine-rich region of RPGR-ORF15 and two AAV inverted terminal repeats (ITRs) were prone to deletions or rearrangements when the plasmid clones were propagated in commonly used bacterial strains. After extensive testing, it was observed that the vector plasmids maintained their integrity in XL10 Gold cells. PCR amplification of the region spanning the repetitive glutamic acid-glycine coding sequence in the mouse or human RPGR-ORF15 cDNA produced the expected 1.3 kb or 1.6 kb fragment in the vector plasmids and all vector preparations. The PCR assay did not identify visible deletion in most AAV vector preparations. However, minor deletions were detected in two vector preparations. The full-length human RPGR-ORF15 vector comprised SEQ ID NO: 15 and encoded the amino acid sequence of SEQ ID NO: 25 (functional variant of wild-type human RPGR). The full-length mouse RPGR-ORF15 vector comprised SEQ ID NO: 24 and encoded the amino acid sequence of SEQ ID NO: 23 (mouse RPGR).

Example 2

This example demonstrates the AAV vector-mediated expression of RPGR-ORF15 proteins.

To test whether the vectors of Example 1 mediate full-length RPGR-ORF15 protein expression in mouse retina, immunoblot analyses of the retinal lysates from vector-treated Rpgr-KO mice were performed. Using an antibody against the C-terminus of the mouse RPGR-ORF15, RPGR protein was identified in the Rpgr-KO retina treated with the AAV8-mRpgr vector. The retinal lysate from an Rpgr-KO mouse injected subretinally with $1 \times 10^9$ vg AAV8-mRpgr vector revealed a ~200 kDa protein band corresponding to the full length RPGR-ORF15 protein, which is identical to that detectable in a wild-type (WT) C57/B16 mouse retina. This protein was identical in size to the wild type (WT) RPGR protein, suggesting the ability of the vector to produce a full-length mouse RPGR-ORF15 protein. Similarly, AAV8-hRPGR vector was able to generate the full-length human RPGR-ORF15 protein in the Rpgr-KO retina. The retinal lysate from an Rpgr-KO mouse injected subretinally with $1 \times 10^9$ vg AAV8-hRPGR vector revealed a ~200 kDa protein band corresponding to the full length RPGR-ORF15 protein, identical to that from a commercially sourced human retinal lysate. No signal was detected in the lane that included 1/10th the amount of retinal lysate from the vector-injected eye, revealing the sensitivity limits of the assay. A set of lower molecular weight proteins in the AAV8-hRPGR-treated retina were also detected when an antibody against the epitopes upstream of the ORF15 exon was employed. Although the possibility that these shorter proteins were caused by the deletions in the ORF15 exon in AAV vector preparations cannot be ruled out, these shorter proteins could also be alternatively spliced or C-terminal truncated forms of RPGR-ORF15, as observed in WT mouse retina (Hong et al., *Invest. Ophthalmol. Vis. Sci.*, 43: 3373-3382 (2002)). Shorter proteins have also been identified in AAV8-mRpgr-treated Rpgr-KO retina when an antibody against the epitopes upstream of the ORF15 exon of mouse RPGR was used.

RPGR-ORF15 protein localizes to the connecting cilia of the photoreceptors in mouse and other mammalian species (Hong et al., *Proc. Natl. Acad. Sci.*, 97: 3649-3654 (2000); Hong et al., *Invest. Ophthalmol. Vis. Sci.*, 44: 2413-2421 (2003)). To test whether the vector-expressed mouse and human RPGR-ORF15 also localize to the connecting cilia, a brief on-slide fixation of frozen retinal section using 1% formaldehyde instead of the conventional 4% paraformaldehyde (PFA) fixation was employed for immunofluorescence assay, since the latter blocks antibody penetration to this region (Hong et al., *Invest. Ophthalmol. Vis. Sci.*, 44: 2413-2421 (2003)). Similar to the WT protein, the vector-expressed RPGR-ORF15 mainly appeared as dots between the inner (IS) and outer segments (OS) corresponding to the location of the connecting cilia. In addition to its connecting cilia localization, the vector-expressed RPGR-ORF15 was frequently observed at the IS, and sometimes at the nuclei and the synaptic terminals of the photoreceptors when the conventional 4% PFA fixation was used. When the modified fixation method was used, RPGR immunostaining was observed at the connecting cilia region in both WT and the AAV8-mRpgr treated retina. When the regular fixation method was used, RPGR was undetectable in the WT retina, but the staining was observed at the IS, ONL and the synaptic region in the AAV8-mRpgr treated retina. This apparent mis-localization of RPGR-ORF15 seems to be vector-related as it was also observed in AAV5 RPGR vector-treated canine retina (Beltran et al., *Proc. Natl. Acad. Sci.*, 109: 2132-2137 (2012)) but not in the WT mouse retina. Without being bound to a particular theory or mechanism, it is believed that overexpression of the protein by using a relatively high vector dose ($1 \times 10^9$ vector genomes (vg)) and a strong RK promoter may account for this observation. No detectable RPGR-ORF15 expression was observed in other retinal layers owing to the photoreceptor specificity of the RK promoter. The mouse Rpgr-ORF15 delivered by the AAV9 vector expressed the protein at a similar level as the AAV8 vector when same dose was used, and the protein was targeted to identical subcellular localization.

Example 3

This example demonstrates the short-term dose-toxicity profile of the mouse and human RPGR-ORF15 vectors.

To define the dose range for a long-term efficacy study, a short-term vector toxicity study was conducted over a 4-month period. Eight week-old Rpgr-KO mice were unilaterally injected with $1 \times 10^{10}$ or $1 \times 10^9$ vg of AAV8-hRPGR or AAV8-mRpgr vector per eye through sub-retinal injection. The fellow eye was used as control by injecting the same volume of vehicle. Dark- and light-adapted ERG were recorded to evaluate responses from rod and cone photoreceptors at 4 months post-injection (PI) before sacrificing the mice for immunofluorescence analyses. Due to the slow retinal degeneration in the Rpgr-KO mouse line, a therapeutic effect at 4 months after vector treatment was not expected.

No statistically significant difference was observed between the vector and the vehicle-treated eyes in ERG amplitudes of dark-adapted a-, b- and light-adapted b-waves in mice that received $1 \times 10^9$ vg AAV8-hRPGR or AAV8-mRpgr vector. However, remarkably lower amplitudes of all three ERG components were observed in eyes receiving $1 \times 10^{10}$ vg vectors, while $1 \times 10^9$ vg/eye vector administration did not cause significant ERG change, indicating the vector toxicity at the high dose. This observation was corroborated by immunofluorescence analyses of the vector-treated retinas. Since the retina sections were fixed in 4% PFA before freezing, only the pool of mis-localized recombinant RPGR at IS was detected (as explained above). More intensive RPGR-ORF15 expression was observed in $1 \times 10^{10}$ vg vector-treated retina, accompanied by a much thinner outer nuclear layer (ONL) and shorter IS. In contrast, the ONL thickness of the $1 \times 10^9$ vg vector-treated retina did not reveal marked difference from the vehicle-treated retina. Both the ERG and immunofluorescence analyses indicate that the dose of $1 \times 10^9$ vg per eye is well tolerated, while $1 \times 10^{10}$ vg is toxic to the mouse retina. Without being bound to a particular theory or mechanism, it is believed that a combinational effect of overexpressing the RPGR-ORF15 protein, the large amount of AAV capsid protein and vector DNA that exceeds the processing capacity of the retinal cells might account for the toxicity of the high vector dose. Therefore, the dose of $1 \times 10^{10}$ vg per eye was not included in the subsequent long-term efficacy study.

Example 4

This example demonstrates the treatment effect in the Rpgr-KO mice following gene delivery of mouse Rpgr-ORF15.

To test whether the mouse Rpgr-ORF15 cDNA delivered by AAV8 or AAV9 vector was efficacious, the vectors were injected in the subretinal space of 6-8 week-old mice at doses ranging from $1 \times 10^8$ to $1 \times 10^9$ vg per eye. Unilateral vector injection was performed on each mouse and the contralateral eye was injected with the vehicle. Due to the slow progression of retinal degeneration in the Rpgr-KO mice (Hong et al., *Proc. Natl. Acad. Sci.*, 97: 3649-3654 (2000); Hong et al., *Invest. Ophthalmol. Vis. Sci.*, 46: 435-441 (2005)), a longitudinal ERG monitoring was performed during the 18-month follow-up period. Given the large variation in ERG amplitudes among individual mice, paired t-test was employed throughout the study to compare the vector- and the vehicle-treated eyes. Among all cohorts, mice receiving $3 \times 10^8$ vg AAV9-mRpgr displayed the strongest therapeutic effect in vector-treated eyes. Although only a slight improvement was observed in the vector-treated eyes at 12 months PI, the therapeutic effect became more pronounced at 18 months PI, in which significantly larger amplitudes were observed for dark-adapted a-wave and light-adapted b-wave in response to increasing intensities of flash stimuli. These eyes also displayed significantly larger dark-adapted b-wave amplitude, which was not seen at 12 months PI, reflecting a better preservation of visual signaling to the bipolar cells. In all seven mice that survived 18 month monitoring, each individual animal exhibited greater dark-adapted a-, b- and light-adapted b-wave amplitudes elicited from the highest flash intensity in the vector-treated eye. Cohorts receiving other vector doses ($1 \times 10^9$ vg/eye AAV8-, $1 \times 10^8$ vg/eye AAV8-, or $1 \times 10^9$ vg/eye AAV9-mRpgr vector) displayed suboptimal rescue at 18 months PI compared with the one receiving $3 \times 10^8$ vg AAV9-mRpgr vector.

Functional rescue of the vector-treated retinas was correlated with their structural improvement. Much thicker ONL was observed in $3 \times 10^8$ vg AAV9-mRpgr treated eyes than the control eyes, as revealed by optical coherence tomography (OCT) retinal imaging at 18 months PI. The increased retinal thickness in the vector-treated eye was observed within a ~1.0 mm² diameter field of view, except for the central area where optic nerve head (ONH) was located. Subsequent to OCT, immunofluorescence analyses of treated mouse retina showed that AAV-mediated RPGR expression spanned roughly half of the cross-section. Vector-treated eyes preserved significantly more rows of photoreceptors than control eyes, consistent with the OCT findings. Seven to ten rows of photoreceptors were maintained in a majority of the vector-treated eyes, compared with four to six rows in the control eyes. The measurements of ONL thickness at 500 μm intervals along the vertical (dorsal-ventral) meridian on retinal sections further corroborated these findings. The average ONL thickness at different locations of the vector-treated retinas ranged between 31.7 μm and 43.5 μm, while it ranged between 19.0 μm and 28.3 μm in the control retinas. The treatment effect appeared to be even more pronounced at 24 months PI in one group of mice receiving $1 \times 10^9$ vg AAV8-mRPGR injection. While the ONL of the control retina almost disappeared in the superior portion and only 1 to 3 rows of photoreceptors remained in the inferior retina, 6-8 rows of photoreceptors survived in inferior areas of the vector-treated retina where RPGR was expressed.

Opsin mis-localization (because of altered transport/targeting to outer segments) is detectable in animal models and in a human carrier with RPGR mutations. Immuno-staining was performed on the $3 \times 10^8$ vg AAV9-mRpgr-treated retina at 18 months PI to assess whether opsin transport could be corrected by Rpgr gene delivery. In the WT retina, M-cone opsin is found exclusively in the outer segments of cone cells. In the vehicle-treated Rpgr-KO retina, M-opsin was detected in inner segments as well as in the perinuclear and synaptic regions in addition to the outer segments. More M-opsin was present in photoreceptor inner segments in the superior retina compared with the inferior retina. Without being bound to a particular theory or mechanism, it is believed that this is probably due to the superior to inferior gradient of M-opsin expression. This M-opsin transport to outer segments was partially rescued in the vector-treated retina at 18 months PI.

Rhodopsin localized only to the rod outer segments in WT retina. This mis-localization was not seen in the RPGR-expressed area in the vector-injected KO retina. Rhodopsin was additionally observed at the IS and perinuclears in the vehicle-injected KO retina. In the young Rpgr-KO mouse retina, rhodopsin was appropriately localized; however, rhodopsin immunostaining was detected in the inner segments and perinuclear region in 20 month-old vehicle-injected Rpgr-KO retina. Rhodopsin localization was corrected in the areas expressing RPGR-ORF15 in the vector-treated retina of Rpgr-KO mice.

Example 5

This example demonstrates the treatment effect in the Rpgr-KO mice following gene delivery of human RPGR-ORF15.

As a potential vector candidate for future human trials, AAV8-hRPGR was tested for its efficacy in Rpgr-KO mice with four different doses; $3 \times 10^9$, $1 \times 10^9$, $3 \times 10^8$ and $1 \times 10^8$ vg per eye. Six to 8 week-old mice were injected with the vector subretinally and ERG was performed at 12 and 18 months PI. Among the four dose groups, optimal outcome was observed in $1 \times 10^9$ vg-treated group. At this dose, the vector-treated eyes displayed significantly higher amplitudes dark-adapted a-, b-wave and light-adapted b-wave were observed in response to increasing intensities of flash stimuli at 18 month PI, indicating the rescue of retinal function in the Rpgr-KO mouse following human RPGR-ORF15 gene delivery. All 11 mice that survived the 18 month monitoring period exhibited higher light-adapted b-wave amplitudes in vector-treated eyes; of these, 10 and 9 mice respectively displayed higher dark-adapted b-wave and dark-adapted a-wave.

Mice receiving $3 \times 10^9$ vg vector demonstrated much lower ERG amplitudes in the vector-treated eyes than control eyes at 18 month PI; however, this difference was not statistically significant at 12 month PI indicating the long-term toxicity at this dose. The $3 \times 10^8$ vg and $1 \times 10^8$ vg vector-treated eyes did not show a difference from control eyes for ERG amplitudes. To investigate whether the therapeutic effect was too small to be detected, ERG was performed again 6 months later when these mice were almost 26 month-old.

ERG improvement was still not observed in the vector-treated eyes in both dose groups, indicating that these two vector doses were too low to achieve functional rescue in the Rpgr-KO mice.

OCT retinal imaging was performed on the Rpgr-KO mice treated with $1 \times 10^9$ vg AAV8-hRPGR vector at 18 months PI. Much thicker ONL, was observed in the vector-treated retinas than the controls, and the thickness of the whole retina in the vector-treated eyes was greater than the controls within ~1.0 mm² diameter field of view. By immunofluorescence analyses, vector-treated retina revealed hRPGR expression in about half of the area of the cross section. Consistent with the OCT findings, more rows of photoreceptors were preserved in the vector-treated retina than in the control and measurements of ONL thickness across 4 mm of retina along the vertical (dorsal-ventral) meridian corroborated these observations. The average ONL thickness at different locations of the vector-treated retinas ranged between 21.2 µm and 33.4 µm, while vehicle-treated retinas had ONL between 14.3 µm and 24.1 µm. Immunofluorescence analyses of the retina receiving a lower vector dose ($3 \times 10^8$ vg) revealed hRPGR staining in a smaller area; however, more photoreceptors were preserved in this area compared to the adjacent region. Therefore, preservation of photoreceptors in vector-transduced areas was still achieved in the lower dose groups despite the lack of overall functional preservation as evaluated by full-field ERG. Rhodopsin was only observed in rod OS of WT retina, but additional staining was observed at the IS, perinuclear and synaptic terminals in the vehicle-treated Rpgr-KO retina. This rhodopsin mis-localization was not detected in areas with appropriate hRPGR expression in the vector-treated ($1 \times 10^9$ vg AAV8-hRPGR) retina, while it was apparent in the control retina.

Example 6

This example demonstrates the rescue of retinal function and structure following RPGR-ORF15 gene delivery to older Rpgr-KO mice.

To assess whether retina with more substantial degeneration would still benefit from the treatment, $3 \times 10^8$ vg AAV8-mRPGR was subretinally injected into 1 year-old Rpgr-KO mice. No appreciable difference was observed between vector- and vehicle-treated eyes when tested at 5 months PI. However, the ERG rescue became apparent in vector-treated eyes at 11 months PI, when mice were 23 month-old. OCT imaging revealed much thicker ONL in the vector-injected retina than in the vehicle-injected control; this finding was subsequently confirmed by morphology analyses. Substantially more rows of photoreceptors were observed in the area with RPGR expression in the vector-injected eye as compared to control retina. These results suggest that the Rpgr-KO mouse could still respond favorably to Rpgr gene delivery even when treated at an advanced age with active degeneration in the retina.

Examples 7-12

The following materials and methods were employed for Examples 7-12: Generation of the Rp2-KO mouse line and animal husbandry An Rp2-KO mouse line was created by crossing an Rp2$^{flox/flox}$ line with a ubiquitous Cre expressing line (CAG cre and Zp3 Cre line). All of the mice were maintained as described in the "mouse line and husbandry" section of the methods described for Examples 1-6 above.

AAV Vector Construction and Production

A synthetic human RP2 cDNA (SEQ ID NO: 1) with ClaI and Xho1 sites was cloned in a vector with a rhodopsin kinase promoter (SEQ ID NO: 10), a chimeric (β-globin/CMV) intron (SEQ ID NO: 9), and a β-globin poly-A tail (SEQ ID NO: 7). AAV type 2 inverted terminal repeats (ITRs) (SEQ ID NOs: 12 and 13) were used in the AAV vector construction. The left ITR (ITR near the promoter region) (SEQ ID NO: 13) was mutated to eliminate the terminal resolution site and AAV D sequence to make it a self-complementary AAV vector.

Triple-plasmid transfection to HEK293 cells was used to produce AAV vectors as described in Grimm et al., *Blood*, 102: 2412-2419 (2003). The self-complementary human RP2 construct (SEQ ID NO: 14) was packaged into an AAV8 capsid (SEQ ID NO: 5). The amount of virus was measured by real time PCR using the following primer and fluorescent labeled probes:

```
Forward primer (5'-3'):
                                        (SEQ ID NO: 20)
-GCACCTTCTTGCCACTCCTA;

Reverse primer (5'-3'):
                                        (SEQ ID NO: 21)
-GACACAGCACCAGGCTAAATCC;
and Probe (5'-3'):
                                        (SEQ ID NO: 22)
-CGTCCTCCGTGACCCCGGC.
```

Sub-Retinal Injection

Subretinal injection was performed as described in Sun et al., *Gene Therapy*, 17: 117-131 (2010) with some modifications. Mice were anesthetized with an intra-peritoneal injection of ketamine (80 mg/Kg) and xylazine (8 mg/Kg). The pupils were dilated with topical atropine (1%) and tropicamide (0.5%). Proparacaine (0.5%) was used as topical anesthesia. Surgery was performed under an ophthalmic surgical microscope. An 18 gauge hypodermic needle was used to make a small incision in the cornea adjacent to the limbus. A 33 gauge blunt needle fitted to a Hamilton syringe was inserted through the incision while avoiding the lens and pushed through the retina. A 1 µl of sample containing either therapeutic vector or a saline solution was delivered subretinally. Therapeutic vectors were given in the right eye and vehicle was given in the fellow eye. Visualization during injection was aided by addition of fluorescein (100 mg/ml AK-FLUOR (fluorescein injection, USP), Alcon, Fort Worth, Tex., USA) to the vector suspensions at 0.1% by volume.

ERG

ERGs were performed using ESPIONE E2 electroretinography system. Mice were dark adapted overnight. Pupils were dilated with topical atropine (1%) and tropicamide (0.5%). The mice were anesthetized with an intra-peritoneal injection of ketamine (80 mg/Kg) and xylazine (8 mg/Kg). All the above procedures were done in dim red light. ERGs were recorded from both eyes using gold wire loops with 0.5% proparacaine topical anesthesia and a drop of 2% methylcellulose for corneal hydration. A gold wire loop placed in the mouth was used as reference, and a ground electrode was placed on the tail. Dark-adapted ERG was done in the dark with brief white flash intensity ranging from −4 log cd-s/m² to +3 log cd-s/m². Light-adapted ERG was recorded after light adaptation of 2 min with white light. ERG recording was done with brief white flash intensity ranging from −0.53 log cd-s/m² to +2 log cd-s/m² with a background white light of 20 cd/m² intensity. The flicker response was taken with 10 Hz light flicks. For recording M and S-opsin mediated ERG response, the mice were first light adapted for 2 minutes in a green light with 20 cd/m² light intensity. ERG was recorded by alternating green and ultraviolet (UV) flash with intensity ranging from −0.52 to +2 log cd-s/m² for green flash and −4 to −0.52 log cd-s/m² for UV flash with a background green illumination of 20 cd/m². ERG was recorded from Rp2-KO mice treated with different vector doses and littermate wild type mice.

Determination of Visual Acuity

Visual acuity of the mice was determined by an optokinetic test in an optokinetic reflex (OKR) arena developed by Cerebral Mechanics following the protocol described in Douglas et al., *Vis. Neurosci.*, 22: 677-684 (2005) and Prusky et al., *Invest. Ophthalmol. Vis. Sci.*, 45: 4611-4616 (2004). Briefly, the mouse was placed in the center of a closed OKR arena surrounded by four computer screens and a camera on top to monitor the movement of the animal. The computer screens created a virtual image of a rotating drum with sine waves grating in a 3D confirmation. The tracking of the gratings by the mouse was scored by its head and neck movement. The spatial frequency of the grating was controlled and monitored by OPTOMOTRY software (Version 14). The maximum spatial frequency in a 100% background contrast which generated a tracking movement by the animal was recorded for each eye.

Immunoblotting

Whole retinal lysate was prepared in RIPA buffer with protease inhibitor cocktail by sonication. The lysate was cleared by centrifugation, and the protein was estimated using Bradford reagent. Approximately 20 μg of protein was used in every lane of 10% denaturing protein gel (BioRad, Hercules, Calif.). Immunoblotting was performed by a standard procedure using the primary antibody against human RP2 and β-actin. The proteins were visualized with peroxidase-conjugated secondary antibody with appropriate reagents.

Immunohistochemistry

For immunohistochemistry, mice were euthanized and eyes were enucleated. The eyes were fixed in 4% PFA solution for 1-2 hours, passed through a series of sucrose solution for cryo-protection, and were flash frozen in OCT solution. A series of retinal sections having a thickness of 12 μm was cut through the eyes in a superior-inferior pole orientation by cryostat. The sections were stained with specific antibody (M & S cone opsin, rhodopsin, PNA, RP2) using the protocol described below. Briefly, sections were blocked in 5% goat serum in PBS containing 0.1% Triton X-100 (PBST) for 1 h, followed by incubation in primary antibodies diluted in 2% goat serum at 4° C. overnight. Sections were washed three times in PBST and incubated with fluorochrome-conjugated secondary antibodies and 0.2 μg/ml DAPI for 1 h. Sections were washed again with PBS and mounted in FLUOROMOUNT-G mounting medium (SouthernBiotech, Birmingham, Ala.). Sections were visualized, and images were captured on a confocal scanning microscope LSM700 (Zeiss, Germany).

To prepare a flat mount, retina enucleated eyes from euthanized mice were first incubated in chilled PBS solution for 15 minutes over ice. Afterwards, eyeballs were then squeezed gently several times to detach the retina. The eyeballs were then fixed in 4% PFA for 1 hour, and the retina was separated from other parts of eye, washed in PBS containing 0.1% Triton, blocked in 5% goat serum in PBST for 4 hrs, followed by incubation in primary antibodies diluted in 2% goat serum at 4° C. overnight. The retina was again washed 3 times (2 for 45 mins each and 1 for 1 hr) in PBST, and incubated with fluorochrome-conjugated secondary antibodies for 4 hrs. The sections were again washed in PBST as described above and mounted in FLUOROMOUNT-G mounting medium (SouthernBiotech, Birmingham, Ala.) with the photoreceptor layers facing up. Images were captured on a confocal scanning microscope LSM700 (Zeiss, Germany).

Statistical Analysis

Two-tailed paired and unpaired t-test was used to compare outcomes in vector-treated versus vehicle-treated eyes. GRAPHPAD Prism 6 software (GraphPad Software, La Jolla, Calif.) was used for statistical analysis.

Example 7

This example demonstrates that a Rp2-KO mouse exhibits a progressive degeneration of cone photoreceptors.

An Rp2-KO mouse model was generated by crossing Rp2$^{flox/flox}$ mice with either a CAG Cre transgenic mouse line as reported in Li et al., *Invest. Ophthalmol. Vis. Sci.*, 54: 4503-4511 (2013) or a ZP3 Cre mouse line. In ZP3-Cre line, Cre is expressed specifically in oocytes. Although Cre is ubiquitously expressed in CAG-Cre line, Cre expression on its own does not affect retinal function, as shown in Li et al., *Invest. Ophthalmol. Vis. Sci.*, 54: 4503-4511 (2013). Addition of CAG-Cre transgene even in the Rp2-KO line has no further impact of the retina. RP2 exon 2 was deleted in the resulting Rp2-KO mouse line, and no RP2 protein was detectable in the retina and other tissues (Li et al., *Invest. Ophthalmol. Vis. Sci.*, 54: 4503-4511 (2013)). To evaluate the progression of retinal degeneration in this model, a large cohort of the mice was monitored along with their wild-type (WT) littermates by electroretinogram (ERG) during an 18-month period. Amplitude of dark-adapted a-wave is mainly contributed by rods. Though cone-derived a-wave is relatively small under light-adapted conditions, b-wave is produced by the inner retina neurons and reflects the activity of cone system. Therefore, dark-adapted a-wave and light-adapted b-wave were used to represent rod and cone functions, respectively. Consistent with previous observations (Li et al., *Invest. Ophthalmol. Vis. Sci.*, 54: 4503-4511 (2013); Zhang et al., *FASEB J.*, 29: 932-942 (2014)), the Rp2-KO mice exhibited significantly reduced amplitudes of dark-adapted a-wave and light-adapted b-wave through the entire duration of the experiments. The stimulus intensities for dark- and light-adapted ERGs were −4.0 to 3.0 and −1.0 to 2.0 log cd s/m², respectively. This ERG amplitude reduction happened even as early as 1 month of age in a small group of monitored mice, indicating functional impairment of both rods and cones at an early age. However, measurement of the ratio of KO to WT for ERG amplitudes revealed distinct dynamics between rod and cone functions in the KO mice over the 18-month period. The dark-adapted a-wave amplitude of KO relative to that of WT remained stable after 4 months of age without additional reduction, whereas the KO to WT ratio of light-adapted b-wave amplitude continuously declined at a nearly constant rate between 4 and 18 months. As a result, about 78% of rod ERG amplitude was preserved at 18 months compared with only 33% of cone ERG amplitude, demonstrating a more severe impairment of cone function in the KO mice. Additionally, the relatively mild impairment in rod function did not significantly impact the inner retina function since no difference was observed between KO and WT mice for dark-adapted b-wave with dim flash intensity. The progressive worsening of cone function in the KO retina was also reflected by the pronounced reduction in the flicker response.

A significant alteration in light-adapted b-wave kinetics was observed in Rp2-KO mice when compared with their WT littermates, consistent with the findings in Zhang et al., FASEB J., 29: 932-942 (2014). To assess the response kinetics, the time it took the b-wave to rise to 50% of its peak amplitude ($T_{50\ rise}$), the time it took to reach the peak amplitude ($T_{max}$, same as implicit time) and the time to fall from the peak to 50% of the peak amplitude ($T_{50}$ decay) were measured. The 4-month-old KO mice displayed significantly longer time course in all three measurements than their WT littermates. In particular, the kinetics of the b-wave falling phase was distinctly slower in KO mice compared with WT, as reflected by much longer $T_{50}$ decay time (40.1±1.6 ms in WT versus 81.8±5.5 ms in KO, mean±SEM). This alteration in kinetics began early, as longer $T_{max}$ and $T_{50}$ decay were already observed in 1-month-old KO mice. The kinetics difference between KO and WT mice appeared to be specific to the cone system, as no such change was observed in dark-adapted b-wave under low flash stimulus intensity, which reflects the function of pure rod system.

Consistent with the cone-mediated ERG findings, very few M- or S-cone photoreceptors were observed at 18 months of age compared with the WT retina, indicating a severe cone degeneration in the Rp2-KO retina. In contrast, no detectable change in the thickness of the rod-dominant photoreceptor layer was seen during the 18-month period. In addition, distribution of rhodopsin in the Rp2-KO mice remained the same as the WT mouse, with rhodopsin mainly being detected at the OS, its natural localization. The thickness of rod-dominant photoreceptor layer was not significantly altered even in the 18-month-old KO retina. The relatively mild rod dysfunction in the KO mice is likely caused by somewhat disorganized OS as revealed by ultrastructural analysis (Li et al., Invest. Ophthalmol. Vis. Sci., 54: 4503-4511 (2013)). Rod disorganization was not captured by light microscopy analyses.

Example 8

This example demonstrates that an AAV8 vector carrying human RP2 cDNA mediates stable RP2 expression in mouse photoreceptors.

To develop gene therapy for RP2-associated retinal degeneration, an AAV vector carrying a human RP2 expression cassette was designed and constructed. The vector (SEQ ID NO: 14) was composed of a photoreceptor-specific human rhodopsin kinase (RK) promoter (SEQ ID NO: 10), a CMV and human β-globin hybrid intron (SEQ ID NO: 9), a human RP2 cDNA (SEQ ID NO: 1), and the human β-globin polyadenylation site (SEQ ID NO: 7), flanked by two inverted terminal repeats (ITRs) from AAV serotype 2 (AAV2) (SEQ ID NOs: 12 and 13). The RK promoter has been shown to be able to drive cell-specific transgene expression in both rods and cones in mice (Khani et al., Invest. Ophthalmol. Vis. Sci., 48: 3954-3961 (2007)). The length of this human RP2 expression cassette was smaller than 2 kilo-basepairs (kb), a size that fit well with a self-complementary (sc) AAV vector that is capable of mediating earlier onset and more efficient transgene expression than a conventional single-stranded (ss) vector. To construct a sc vector, one WT ITR was replaced with a mutant ITR in which the terminal resolution site and the AAV D sequence were deleted. The vector was packaged into AAV8 (SEQ ID NO: 5), a serotype that transduces photoreceptors of mouse and non-human primate very efficiently, and was designated as AAV8-scRK-hRP2 vector (SEQ ID NO: 14), encoding the amino acid sequence of SEQ ID NO: 2 (human RP2).

To test whether the vector mediates human RP2 expression, the vector was injected subretinally into RP2-KO mice, and the retinal extracts were subjected to immunoblot analyses 4 weeks later with a polyclonal antibody recognizing both mouse and human RP2 proteins. While the vehicle-treated retina did not reveal any RP2-specific band, the vector-treated retina exhibited a band at the expected molecular weight of ~40 kDa, identical to that of the human retinal lysate, indicating the vector's ability to express human RP2 protein. The endogenous mouse RP2 protein in the WT retina migrated slightly faster than the human counterpart. Without being bound to a particular theory or mechanism, it is believed that because mouse and human RP2 proteins contain similar numbers of amino acid residues (a.a.) (350 a.a. for human RP2 and 347 a.a. for mouse RP2), this electrophoretic mobility difference might reflect the different amino acid compositions and/or post-translational modifications of the two proteins.

Immunofluorescence analysis was performed to examine the cellular and subcellular localization of the vector-expressed RP2 protein in the retina. Endogenous mouse RP2 protein was detected in multiple layers in WT retina, including the IS, outer and inner plexiform layers (OPL, and IPL), which was not seen in the Rp2-KO retina. The vector-expressed human RP2 protein was primarily localized at the IS and nuclei of photoreceptors, but was not observed in any other layers of the retina. Without being bound to a particular theory or mechanism, it is believed that this is probably due to the specificity of the RK promoter and the inaccessibility of the vector to the inner retinal layers following subretinal administration. The vector-mediated RP2 expression was sustained throughout the entire 18-month study period without detectable loss. No expression of RP2 protein was detected in Rp2-KO mice injected with vehicle.

Example 9

This example demonstrates that RP2 gene delivery with a wide dose range rescues cone function in Rp2-KO mice.

To test the treatment effect of the AAV8-scRK-hRP2 vector, 4 to 6 week-old Rp2-KO mice were administered subretinally with the vector at three doses; $1 \times 10^8$, $3 \times 10^8$ and $1 \times 10^9$ vector genomes (vg) per eye. The mice received unilateral vector injections, with the contralateral eyes receiving vehicle injections as controls. A longitudinal ERG monitoring was performed until the mice reached 18 months of age. Given the large variation in ERG amplitudes among individual mice, paired t-test was employed throughout the study to compare the vector- and the vehicle-treated eyes. Cone function rescue was achieved in the $1 \times 10^8$ and the $3 \times 10^8$ vg/eye dose groups as reflected by the significantly higher light-adapted ERG b-wave amplitude in vector-treated eyes as compared to vehicle-injected fellow eyes. This therapeutic effect was observed as early as at 4 months of age, the earliest time point of examination, and it lasted through the entire duration of the study period. Almost 75% (71-78%) of photopic b-wave amplitude was preserved in vector-treated eyes at 18 months in contrast to only ~28% remaining in the control eyes. In addition to preservation of light-adapted b-wave amplitude, the treatment completely corrected the alteration of b-wave kinetics in the KO retina, as revealed by nearly normal $T_{50}$ rise, $T_{max}$ and $T_{50}$ decay measured in the vector-treated eyes of 4-month-old mice.

The 1×10$^8$ vg/eye vector treatment appeared not to be toxic to rods, as no significant difference was observed between vector- and vehicle-treated eyes in rod ERG response (dark-adapted a-wave) during the 18-month study period. Similarly, 3×10$^8$ vg/eye vector treatment had no obvious effect on rods in general, although slightly lower dark-adapted response was observed at certain time points. The lack of effect on rods may be explained by early onset (within 1 month of age and before vector administration, data not shown), through slower progression of functional impairment in rods of Rp2-KO mice.

The effectiveness of 1×10$^8$ and 3×10$^8$ vg/eye vector treatment prompted exploration into whether a lower dose could still be functional. Therefore, the vector was administered to one group of mice at a dose of 5×10$^7$ vg/eye, and the treated mice were examined by ERG at 6.5 and 18 months of age. Significantly higher light-adapted b-wave amplitude was observed in the vector-treated eyes as compared to the control eyes, indicating the vector's potency at this low dose. The cone function rescue was not biased toward M- or S-cones, since the vector-treated eyes displayed comparable preservation of M- and S-cone-driven ERG responses.

To determine if RP2 gene delivery could result in a better visual acuity, mice treated with 1×10$^8$ vg or 3×10$^8$ vg vector were subjected to an optokinetic test under photopic conditions at 19 months of age. Although lower than WT controls, the visual acuity of the vector-treated eyes was significantly higher than that of the vehicle-treated eyes, indicating an improvement in cone-mediated visual behavior in RP2-KO mice by the treatment.

Example 10

This example demonstrates that RP2 gene delivery with a wide dose range rescues cone function in Rp2-KO mice.

M-opsin localized to OS in WT cones but was found mis-localized to IS, peri-nuclei, and synaptic terminals in vehicle-treated Rp2-KO cones, consistent with previous findings (Li et al., *Invest. Ophthalmol. Vis. Sci.*, 54: 4503-4511 (2013)). In addition, the number of M-cones in vehicle-treated KO retina appeared to be reduced at 6.5 months of age compared to WT retina, indicating substantial cone degeneration. However, in vector treated-retina, the M-opsin mis-localization was alleviated, and more M-cone cells were preserved. Normal subcellular localization of M-opsin was observed in vector-treated retina, suggesting that the treatment either prevented or reversed M-cone mis-trafficking. Similarly, more S-cones were observed in vector-treated retina, although no detectable S-opsin mis-localization was seen in either vehicle or vector-treated KO eyes. Consistent with the findings of Zhang et al., *FASEB J.*, 29(3):932-42 (2015), cone PDE6 expression were almost undetectable in the outer segments of vehicle-treated Rp2-KO retina, whereas vector-treated retina retained near normal expression of the protein in the outer-segments. Localizations of two rod-specific proteins, rhodopsin and PDE6β, were also examined. These two proteins were mainly localized at the OS of photoreceptors in WT retina, and their expression or localization in KO retina was not affected by vector treatment.

Cone rescue was more pronounced in the treated eyes at the final 18-month time point, as revealed by a significantly higher number of peanut agglutinin (PNA)-stained cells in both superior and inferior retina compared with those of the control eyes. Immunofluorescence analyses of both retinal whole-mounts and sections revealed significantly higher number of M- and S-cones in vector-treated KO retina than the vehicle-treated retina.

Example 11

This example demonstrates that late RP2 gene delivery maintains cone function and viability in Rp2-KO mice.

Impairment of cone function starts before 1-month of age m the Rp2-KO mouse model (Example 7; Li et al., *Invest. Ophthalmol. Vis. Sci.*, 54: 4503-4511 (2013)). To assess whether Rp2-KO mice with more advanced cone dysfunction would still benefit from the treatment, the vector was administered to 10-month old Rp2-KO mice at a dose of 3×10$^8$ vg/eye, and their retinal function and structure was examined when they reached 18-month of age. The vector-treated eyes displayed significantly higher light-adapted b-wave amplitude than vehicle-treated eyes as compared to vehicle-treated eyes, although no difference was seen in rod ERG. Consistent with this, substantial M- and S-opsin and cone PDE6-expressing cells were observed in the vector-treated retina, in contrast to the vehicle-treated retina.

Example 12

This example demonstrates an effective dosage of the RP2 vector for use in Rp2-KO mice.

Vector doses ranging from 5×10$^7$ to 3×10$^4$ vg/eye were found to be efficacious in rescuing the function and viability of cone photoreceptors in Rp2-KO mice, as described above. These doses did not seem to affect rod function during the 18-month study period, although slight reductions were seen at 8 and 12 months in the 3×10$^8$ vg dose group. Most toxicity was confined to the dark-adapted ERG response, indicating transient toxicity of the vector at this dose towards rods. However, cone function was significantly improved at the dose of 3×10$^8$ vg. In contrast, mice that received the dose of 1×10$^9$ vg/eye exhibited significantly impaired rod function at all the time points of ERG examination (4 months, 8 months, and 18 months), as reflected by remarkably reduced amplitudes of dark-adapted a- and b-waves. Although this dose preserved cone function at 4 and 8 months, this treatment benefit eventually diminished at 18 months. Without being bound to a particular theory or mechanism, it is believed that this is probably due to secondary cone cell death caused by eventual loss of rods. Immunofluorescence analysis of retinal sections at the final 18-month time point revealed much thinner or even diminished outer nuclear layer at multiple regions in the 1×10$^9$ vg-treated eye, in contrast to no obvious changes in the 1×10$^8$ vg-treated eye. Therefore, the dose of 1×10$^9$ vg/eye was toxic to the retina.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising,"

"having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An adeno-associated virus (AAV) vector comprising a nucleic acid comprising
   (a) a nucleotide sequence encoding RP2 or a functional fragment thereof;
   (b) a human β-globin polyadenylation signal or a functional fragment thereof;
   (c) a cytomegalovirus (CMV)/human β-globin intron;
   (d) a human rhodopsin kinase promoter comprising the nucleotide sequence of SEQ ID NO: 10; and
   (e) an AAV2 Inverted Terminal Repeat (ITR) or a functional fragment thereof;
   wherein the nucleotide sequence encoding RP2 or functional fragment thereof is under the transcriptional control of the rhodopsin kinase promoter.

2. The vector of claim 1, comprising the nucleotide sequence of SEQ ID NO: 7.

3. The vector of claim 1, comprising the nucleotide sequence of SEQ ID NO: 9.

4. The vector according to claim 1, wherein the vector is self-complementary.

5. The vector according to claim 1, wherein the vector is an AAV8 or AAV9 vector.

6. A pharmaceutical composition comprising the vector of claim 1, further comprising a pharmaceutically acceptable carrier.

7. A method of treating or preventing X-linked retinitis pigmentosa (XLRP) in a mammal in need thereof, the method comprising administering to the mammal the vector of claim 1 in an amount effective to treat or prevent XLRP in the mammal.

8. A method of increasing photoreceptor number in a retina of a mammal, the method comprising administering to the mammal the vector of claim 1 in an amount effective to increase photoreceptor number in the retina of the mammal.

9. A method of increasing visual acuity of a mammal, the method comprising administering to the mammal the vector claim 1 in an amount effective to increase visual acuity in the mammal.

10. A method of decreasing retinal detachment in a mammal, the method comprising administering to the mammal the vector of claim 1 in an amount effective to decrease retinal detachment in the mammal.

11. A method of increasing the electrical response of a photoreceptor in a mammal, the method comprising administering to the mammal the vector of claim 1 in an amount effective to increase the electrical response of the photoreceptor in the mammal.

12. A method of increasing expression of RP2 in a retina of a mammal, the method comprising administering to the mammal the vector of claim 1 in an amount effective to increase expression of RP2 in the retina of the mammal.

13. The method of claim 12, comprising administering the vector comprising the nucleotide sequence encoding RP2 at a dose of about $5 \times 10^6$ to about $5 \times 10^{12}$ vector genomes (vg) per eye.

14. The method of claim 12, wherein the mammal is a human.

15. The vector according to claim 1, comprising the nucleotide sequence of SEQ ID NO: 12.

16. The vector according to claim 1, comprising the nucleotide sequence of SEQ ID NO: 13.

17. The vector according to claim 1, comprising the nucleotide sequence of SEQ ID NO: 1.

18. The vector according to claim 1, wherein the nucleotide sequence encodes an amino acid sequence comprising SEQ ID NO: 2.

19. An adeno-associated virus (AAV) vector comprising a nucleic acid comprising
   (a) a nucleotide sequence encoding RP2 or a functional fragment thereof;
   (b) a human β-globin polyadenylation signal or a functional fragment thereof;
   (c) a cytomegalovirus (CMV)/human β-globin intron comprising the nucleotide sequence of SEQ ID NO: 9;
   (d) a human rhodopsin kinase promoter; and
   (e) an AAV2 Inverted Terminal Repeat (ITR) or a functional fragment thereof;
   wherein the nucleotide sequence encoding RP2 or functional fragment thereof is under the transcriptional control of the rhodopsin kinase promoter.

20. The vector according to claim 19, wherein the vector is an AAV8 or AAV9 vector.

21. A pharmaceutical composition comprising the vector of claim 19, further comprising a pharmaceutically acceptable carrier.

22. An adeno-associated virus (AAV) vector comprising a nucleic acid comprising
   (a) a nucleotide sequence encoding RP2 or a functional fragment thereof;
   (b) a human β-globin polyadenylation signal or a functional fragment thereof;
   (c) a cytomegalovirus (CMV)/human β-globin intron;
   (d) a human rhodopsin kinase promoter; and
   (e) an AAV2 Inverted Terminal Repeat (ITR) or a functional fragment thereof;
   wherein the nucleotide sequence encoding RP2 or functional fragment thereof is under the transcriptional control of the rhodopsin kinase promoter and the AAV vector comprises a nucleotide sequence that has at least 90% sequence identity to SEQ ID NO: 14.

23. The vector according to claim 22, comprising a nucleotide sequence that has at least 95% sequence identity to SEQ ID NO: 14.

24. The vector according to claim 22, comprising the nucleotide sequence of SEQ ID NO: 14.

25. The vector according to claim 22, wherein the vector is an AAV8 or AAV9 vector.

* * * * *